United States Patent
Zhi

(10) Patent No.: US 10,441,567 B2
(45) Date of Patent: Oct. 15, 2019

(54) METHODS AND COMPOSITIONS FOR MODULATING HORMONE LEVELS

(71) Applicant: Ligand Pharmaceuticals Incorporated, San Diego, CA (US)

(72) Inventor: Lin Zhi, San Diego, CA (US)

(73) Assignee: LIGAND PHARMACEUTICALS INCORPORATED, San Diego, CA (US)

(*) Notice: Subject to any disclaimer, the term of this patent is extended or adjusted under 35 U.S.C. 154(b) by 0 days.

(21) Appl. No.: 15/111,741

(22) PCT Filed: Jan. 14, 2015

(86) PCT No.: PCT/US2015/011415
§ 371 (c)(1),
(2) Date: Jul. 14, 2016

(87) PCT Pub. No.: WO2015/108988
PCT Pub. Date: Jul. 23, 2015

(65) Prior Publication Data
US 2016/0338995 A1   Nov. 24, 2016

Related U.S. Application Data

(60) Provisional application No. 61/928,551, filed on Jan. 17, 2014.

(51) Int. Cl.
| | | |
|---|---|---|
| A61K 9/00 | (2006.01) | |
| A61K 31/40 | (2006.01) | |
| A61K 31/47 | (2006.01) | |
| A61K 31/58 | (2006.01) | |
| A61K 45/06 | (2006.01) | |
| A61K 31/138 | (2006.01) | |
| A61K 31/277 | (2006.01) | |
| A61K 31/402 | (2006.01) | |
| A61K 31/473 | (2006.01) | |
| A61K 31/567 | (2006.01) | |
| A61K 31/4535 | (2006.01) | |

(52) U.S. Cl.
CPC .......... *A61K 31/40* (2013.01); *A61K 9/0014* (2013.01); *A61K 9/0019* (2013.01); *A61K 9/0053* (2013.01); *A61K 31/138* (2013.01); *A61K 31/277* (2013.01); *A61K 31/402* (2013.01); *A61K 31/4535* (2013.01); *A61K 31/473* (2013.01); *A61K 31/567* (2013.01); *A61K 31/58* (2013.01); *A61K 45/06* (2013.01); *A61K 31/47* (2013.01)

(58) Field of Classification Search
CPC .................. A61K 31/47; A61K 31/40
USPC ................................. 514/312, 429
See application file for complete search history.

(56) References Cited

U.S. PATENT DOCUMENTS

| | | | | |
|---|---|---|---|---|
| 3,710,795 | A | 1/1973 | Higuchi et al. | |
| 4,044,126 | A | 8/1977 | Cook et al. | |
| 7,622,592 | B2 * | 11/2009 | Kim | C07D 401/04 548/181 |
| 7,816,372 | B2 * | 10/2010 | Zhi | C07D 401/04 514/312 |
| 8,354,446 | B2 * | 1/2013 | Zhi | C07D 207/08 514/429 |
| 8,501,690 | B2 * | 8/2013 | Stark | A61K 31/138 514/9.7 |
| 2006/0019989 | A1 | 1/2006 | Steiner et al. | |
| 2012/0004220 | A9 | 1/2012 | Zhi | |

FOREIGN PATENT DOCUMENTS

WO   WO 2006/010162   1/2006

OTHER PUBLICATIONS

Bart L Clarke et al. "New Selective Estrogen and Androgen Receptor Modulators" Current Opinion in Rheumatology, vol. 21, No. 4, Jul. 1, 2009.
H Huynh et al. "Co-administration of inasteride and the pure anti-oestrogen ICI 182,780 act synergistically in modulating the IGF system in rat prostate" Journal of Endocrinology, vol. 171, No. 1, Oct. 1, 2001.
Maneesh N Singh et al. "The Multiple Applications of Tamoxifen: an Example Pointing to SERM Modulation being the Aspirin of the 21st century" Jan. 1, 2008. Retrieved from the Internet on May 17, 2017. http://www.medsckimonit.com/download/getfreepdf/1/EN.
Rajeev Kumar et al. "Selective estrogen receptor modulators regulate stromal proliferation in human benign prostatic hyperplasia by multiple beneficial mechanisms-action of two new agents" Investigational New Drugs., vol. 30, No. 2, Dec. 23, 2010.
Staiman V R et al. "Tamoxifen for Flutamid/Finasteride-induced Gynecomastia", Urology, Belle Mead, NJ, US, vol. 50, No. 6, Jan. 1, 1997.
International Search Report and Written Opinion dated Jun. 25, 2015 issued corresponding PCT/US15/11415.
Partial Supplementary European Search Report dated May 30, 2017 issued in corresponding EP 15737091.7.
Extended European search report dated Sep. 7, 2017 issued in corresponding EP 15737091.7.

* cited by examiner

*Primary Examiner* — Kevin E Weddington
(74) *Attorney, Agent, or Firm* — Knobbe, Martens, Olson & Bear LLP

(57) ABSTRACT

Provided herein are compositions and methods for the treatment of androgen and estrogen receptors mediated conditions. Specifically, a composition that includes an effective amount of a selective estrogen receptor modulator (SERM) and an effective amount of a 5a-reductase inhibitor, or a pharmaceutically acceptable salt, ester or prodrug of the foregoing is provided. Also provided are methods for the treatment of aging related conditions and diseases.

4 Claims, 1 Drawing Sheet

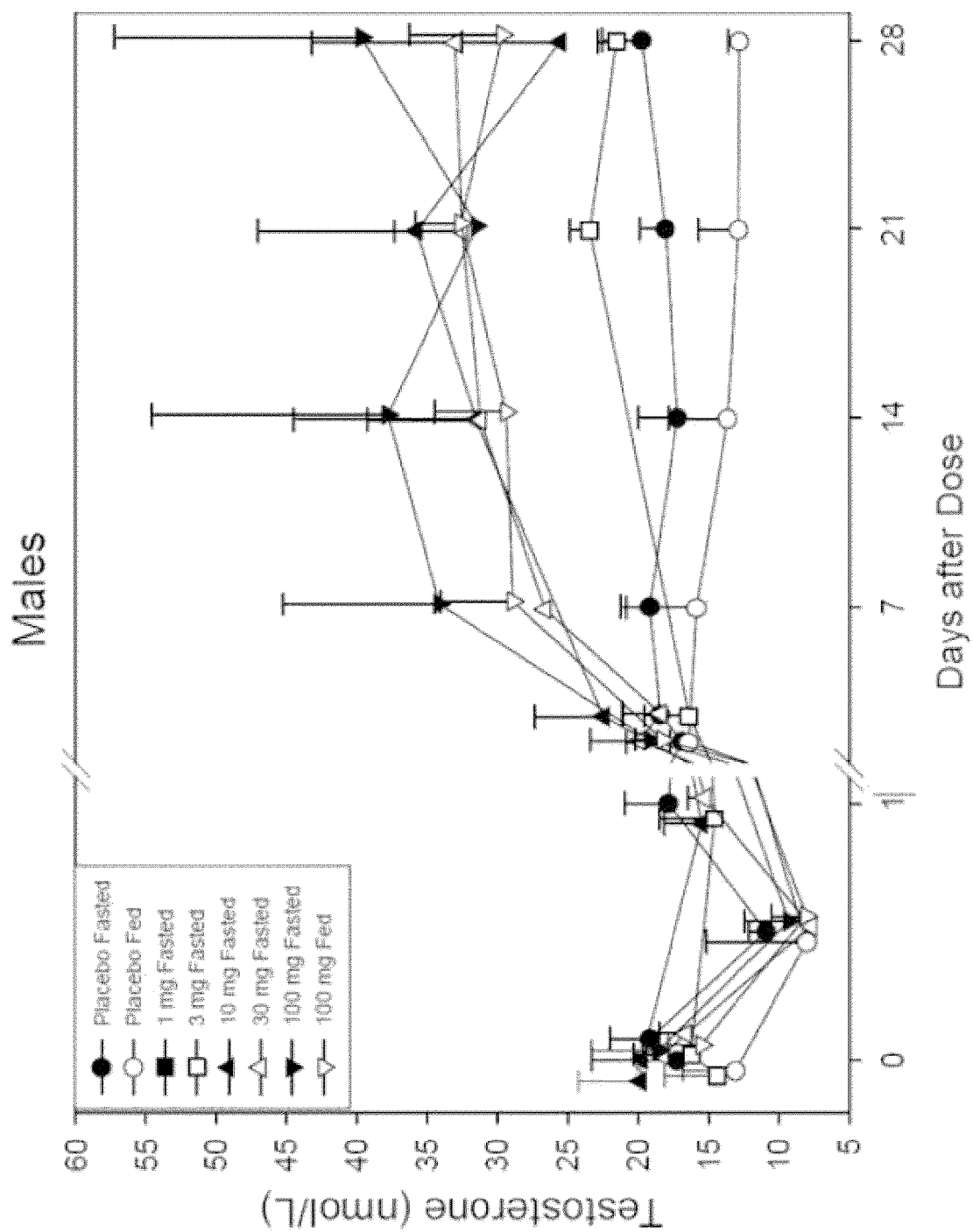

METHODS AND COMPOSITIONS FOR MODULATING HORMONE LEVELS

FIELD

Provided herein are compositions and methods for the treatment of androgen and/or estrogen receptor mediated conditions and diseases. Also provided are methods for the treatment of aging related conditions and diseases. Also provided are compositions including therapeutic compound classes for the treatments.

BACKGROUND

Estrogens and androgens are sex hormones that play essential roles in sex diferenciation, maturation, and reproductive functions of both men and women. Sex hormone levels increase significantly at puberty and maintain a relative constant level till the sudden drop at menopause for women and gradual decline for men after late 40s of age. There are many target organs of the two hormones beyond the sex organs. In women's health at and after menopause, effects of estrogens in uterus, breasts, vagina, CNS, bone, and cardiovascular system are mostly concerned. In men's health at and after andropause, effects of androgens in prostate, CNS, muscle, bone, and cardiovascular system are mainly concerned.

Hormone replacement therapy (HRT), used to refer to female hormone therapy for menopausal women, had been widely used for treatment of menopausal symptoms and prevention of aging related diseases till the unexpected benefit/risk results of Women's Health Initiative (WHI) trials were published (A. L. Hersh, et al. JAMA 291(1):47-53 (2004)). Although population of menopausal women and life expectancy continue to increase, the therapeutic options dealing with menopausal symptoms and aging related chronical diseases are limited due to the unclear cardiovascular outcomes of available therapies.

First generation therapeutic female hormones represented by Premarin have clinical benefits on CNS (reduction of hot flashes), bone (prevention of osteoporosis), breasts (prevention of breast cancer), and vagina (reduction in vaginal atrophy), clinical risk in uterus (increase cancer incidence), and complex benefit/risk effects on cardiovascular system (increase of blood clots and improvement of lipid profile). Progestin was combined with estrogens such as Prempro to counter the uterus effect of estrogens. Unfortunately, the synthetic progestin also counter the beneficial breasts effect of estrogens and add negative effects on cardiovascular system. Selective estrogen receptor modulators (SERMs) have mixed agonist/antagonist activities in different tissues and been developed to avoid the negative uterus effect of estrogens but loss the benefit in CNS. Since SERMs enhance the benefit effect of estrogens in the breasts, they are widely used to treat and prevent estrogen receptor(ER)-positive breast cancer. A combination therapy, Duavee™, of estrogens and SERM (bazedoxifene) was recently approved by US FDA for the treatment of menopausal symptoms and the prevention of postmenopausal osteoporosis. Bazedoxifene blocks the negative uterus effect of estrogens and estrogens compensate the CNS effect that SERMs do not have. ERs have complex relationship with cardiovascular system due to the indirect and multifactor effects. Cardiovascular outcome of a specific ER modulating compound depends on many factors including receptor selective profile, route of administration, lipid modulating profile, patient age, treatment history, and cardiovascular risk factors, which generates great challenge in new drug development to boost cardiovascular benefit/risk ratio.

Androgen therapy has been used to treat a variety of male disorders such as reproductive disorders and primary or secondary male hypogonadism. A number of natural or synthetic androgens have been investigated for the treatment of musculoskeletal disorders, such as bone disease, hematopoietic disorders, neuromuscular disease, rheumatological disease, wasting disease, and for hormone replacement therapy, such as female androgen deficiency. Testosterone (T) is available in several different forms including injection, patch, and gel for the treatment of hypogonadism. Testosterone therapy offers benefits on CNS (such as libido), muscle (improvement in BMI), and bone (prevention/treatment of osteoporosis), but is associated with increased risk in prostate (BPH, prostate cancer) and cardiovascular system (e.g. see B. Shehzad, et al. NEJM 363(2): 109-22 (2010)).

Selective androgen receptor modulators (SARMs) are designed to separate anabolic and androgenic activities of androgens. Androgenic activity of T in prostate and sebaceous glands is achieved by converting to biologically more active dihydrotestosterone (DHT) via tissue-selectively expressed enzymes, 5α-reductases. Inhibitors of 5α-reductases such as finasteride and dutasteride are used to block androgen effects in prostate and sebaceous glands. Combination of a 5α-reductase inhibitor and T supplement regimen can potentially offer T benefit in CNS with lower risk to develop BPH or prostate cancer in older patients (e.g. see A. Meehan. US 2009/0123571). SARMs are typically not substrates of 5-alpha-reductase and have good selectivity towards muscle, bone, and CNS over prostate and sebaceous glands based on the non-reductable mechanism alone. However, SARMs are not designed to mitigate negative cardiovascular effects of androgens, which results in concerns of developing SARMs for long-term use despite of their demonstrated benefits on muscle, bone, and CNS.

Humans need both estrogens and androgens with different ratios in males and females. Endogenous estrogens and androgens are generated in the same biosynthetic pathways and their levels are tightly controlled by the gonadal feedback mechanism. Androgens have a negative feed-back mechanism and biosynthesis of androgens decrease when their circulation level increases. It has been noticed that endogenous androgen level and androgen supplements have different effects on cardiovascular systems. It has been hypothesized that negative cardiovascular outcome of androgens is negatively correlated with endogenous androgen production and thus the negative impact of exogenous androgens on cardiovascular system may be related to block endogenous androgen production through the feed-back mechanism (e.g. see L. Zhi. WO 2013/134311). Estrogens have a dual feed-back mechanism where negative feed-back mechanism works at lower levels and positive feed-back mechanism dominates at high levels. As a result, the effect of exogenous estrogens on cardiovascular system is more complicated than that of androgens. Therapeutic intervention of the gonadal feed-back system can manipulate endogenous hormone production. Gonadotropin-releasing hormone receptor antagonists and agonists are clinically used to shut down endogenous sex hormone production as referred to as "chemical castration". Some SERM compounds have demonstrated activity to increase luteinizing hormone (LH) secretion in men, which leads to increase in endogenous T production (e.g. see V. Birzniece, et al. JCEM 95(12): 5443-8 (2010)). Enclomiphene is currently developed as a potential oral "T therapy" for hypogonadism (R. Wiehle, et al. BJUI 112: 1188-200 (2013)).

Steroid hormone binding globulin (SHBG) is a glycoprotein that binds to androgens and estrogens in circulation and, as a result, reduces the hormone levels that are available for binding to their target hormone receptors. SHBG is produced in the liver and affected by the hormone levels in the liver. Estrogen supplements and SERMs generally increase the production of SHBG, especially when they are administrated via oral route. Androgen supplements and SARMs tend to decrease SHBG production. Since SHBG level affects biologically available sex hormone levels, biological activity of the hormones can be affected by the effects of supplemental hormones on SHBG.

Estrogens are biosynthesized from androgens by aromatase. T therapy may provide additional benefit of estrogens through the aromatase conversion (e.g. see J. S. Finkelstein, et al. NEJM 369: 1011-22 (2013)). Estrogen therapies lacking androgen component and SARMs lacking estrogen component may not be a complete hormone profile replacement.

Hormone therapies that can address all of the major concerns of risk factors are in a great need for rapidly growing aging population. It is among the objects herein to provide such methods and compositions that combine existing therapeutic classes to address the broader safety issues of the currently available therapies.

SUMMARY

Some embodiments disclosed herein relate generally to methods and compositions for treating of a condition and/or a disease related to androgen and/or estrogen receptors by modulating the activity of the androgen and/or estrogen receptors.

Some embodiments disclosed herein relate generally to a composition that can include an effective amount of a selective estrogen receptor modulator (SERM) and an effective amount of a 5α-reductase inhibitor, or a pharmaceutically acceptable salt, ester or prodrug of the foregoing. Other embodiments disclosed herein relate generally to a composition that can include an effective amount of a selective androgen receptor modulator compound (SARM) and an effective amount of an estrogen receptor modulator, or a pharmaceutically acceptable salt, ester or prodrug of the foregoing.

Other embodiments disclosed herein relate generally to a method for replacing testosterone in a male subject that can include administering to the male subject an effective amount of laxofoxifene, or a pharmaceutically acceptable salt, ester or prodrug thereof, wherein the administration of laxofoxifene, or a pharmaceutically acceptable salt, ester or prodrug thereof, of increases the amount of testosterone in the male subject.

BRIEF DESCRIPTION OF THE DRAWINGS

FIG. 1 shows the total serum T level over a period of 28 days after administration of single dose lasofoxifene in male subjects.

A. DEFINITIONS

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

It is to be understood that both the foregoing general description and the following detailed description are exemplary and explanatory only and are not restrictive of the subject matter claimed. In this application, the use of the singular includes the plural unless specifically stated otherwise. In this application, the use of "or" means "and/or" unless stated otherwise. Furthermore, use of the term "including" as well as other forms, such as "includes," and "included" is not limiting.

As used herein, ranges and amounts can be expressed as "about" a particular value or range. "About" also includes the exact amount. Hence "about 10%" means "about 10%" and also "10%."

As used herein, "optional" or "optionally" means that the subsequently described event or circumstance does or does not occur, and that the description includes instances where the event or circumstance occurs and instances where it does not. For example, an optionally substituted group means that the group is unsubstituted or is substituted.

As used herein, the singular forms "a," "an" and "the" include plural referents unless the context clearly dictates otherwise. Thus, for example, reference to a composition comprising "a therapeutic agent" includes compositions with one or a plurality of therapeutic agents.

As used herein, the terms "treat" and "treating" encompass either or both responsive and prophylaxis measures, e.g., designed to inhibit, slow or delay the onset of a symptom of a disease or disorder, achieve a full or partial reduction of a symptom or disease state, and/or to alleviate, ameliorate, lessen, or cure a disease or disorder and/or its symptoms. The term treatment also is intended to include prophylactic treatment.

As used herein, the term "treatment" means any manner in which the symptoms of a condition, disorder or disease are ameliorated or otherwise beneficially altered. Hence, treatment encompasses prophylaxis, therapy and/or cure. Treatment also encompasses any pharmaceutical use of the compositions herein.

As used herein, amelioration of the symptoms of a particular disease or disorder by a treatment, such as by administration of a compound provided herein or a pharmaceutical composition thereof or other therapeutic agent, refers to any lessening, whether permanent or temporary, lasting or transient, of the symptoms that can be attributed to or associated with administration of the composition or therapeutic.

As used herein, prevention or prophylaxis refers to methods in which the risk of developing disease or condition is reduced. Prophylaxis includes reduction in the risk of developing a disease or condition and/or a prevention of worsening of symptoms or progression of a disease or reduction in the risk of worsening of symptoms or progression of a disease.

As used herein, the term "therapeutic agent" refers to conventional drugs and drug therapies, including vaccines, which are known to those skilled in the art.

As used herein, an "effective amount" of a compound or composition for treating a particular disease is an amount that is sufficient to ameliorate, or in some manner reduce the symptoms associated with the disease. Such amount can be administered as a single dosage or can be administered according to a regimen, whereby it is effective. The amount can cure the disease and/or ameliorate one or more symptoms of the disease and/or condition. Repeated administration may be needed to achieve a desired result (e.g., treatment of the disease and/or condition).

As used herein, "therapeutically effective amount" or "therapeutically effective dose" refers to an agent, compound, material, or composition containing a compound that is at least sufficient to produce a therapeutic effect. An "effective amount" is the quantity of a therapeutic agent necessary for preventing, curing, ameliorating, arresting or partially arresting a symptom of a disease or disorder.

As used herein, the term "target receptor" refers to a molecule or a portion of a receptor capable of being bound by a selective binding compound. In some embodiments, a target receptor can be an androgen receptor. In some embodiments, a target receptor can be an estrogen receptor.

As used herein, the term "selective binding compound" refers to a compound that selectively binds to any portion of one or more target receptors.

As used herein, the term "selectively binds" refers to the ability of a selective binding compound to bind to a target receptor with greater affinity than it binds to a non-target receptor. In some embodiments, specific binding refers to binding to a target with an affinity that is at least 2, 5, 10, 25, 50, 75, 100, 150, 200, 250, 500, 1000 or more times greater than the affinity for a non-target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In some embodiments, a modulator can be an inhibitor, which decreases the magnitude of one or more activities of a molecule. In some embodiments, an inhibitor can completely prevents one or more activities of a molecule. In other embodiments, a modulator can be an activator, which increases the magnitude of at least one activity of a molecule. In some embodiments, the presence of a modulator can result in an activity that does not occur in the absence of the modulator.

As used herein, the term "selectively modulates" refers to the ability of a selective modulator to modulate a target activity to a greater extent than it modulates a non-target activity. In some embodiments the target activity can be selectively modulated by, for example about or 2 fold up to more than about or 500 fold, in some embodiments, about or 2, 5, 10, 25, 50, 75, 100, 150, 200, 250, 300, 350, 400, 450 or more than 500 fold.

As used herein, the term "tissue-selective" refers to the ability of a compound to modulate a biological activity in one tissue to a greater or lesser degree than it modulates a biological activity in another tissue. The biological activities in the different tissues can be the same or they can be different. The biological activities in the different tissues can be mediated by the same type of target receptor. In some embodiments, e.g., a tissue-selective compound can modulate an AR mediated biological activity in one tissue and fail to modulate, or modulate to a lesser degree, an AR mediated biological activity in another tissue type.

As used herein, "selective androgen receptor modulator" or "SARM" is a compound that mimics the action of a natural androgen receptor ligand in some tissues but not in others. SARMs are compounds that elicit androgen agonism in one or more target tissues (e.g., muscle, CNS, and/or bone) and antagonism and/or minimal agonism or no effect in other tissues (e.g., skin, prostate). SARMs can exhibit tissue selective androgen receptor agonism. SARMs can exhibit agonistic anabolic properties and antagonistic androgenic properties in selected tissues. For example, SARMs can display tissue selective anabolic activities in muscle, bone, and CNS with reduced androgenic activities in prostate and sebaceous glands. Others SARMs are AR agonists in some tissues and can cause increased transcription of AR-responsive genes (e.g., muscle anabolic effect). In other tissues, SARMS can be competitive inhibitors of androgens, such as testosterone, on the androgen receptor (AR) and thereby prevent agonistic effects of the native androgens. For example, compounds provided herein that are SARMs can have agonist activity in muscle and demonstrate antagonist activity in a gonad of a subject. SARMs that demonstrate such activity can increase muscle mass and decrease fat in subjects without causing androgenic side effects, such as sebaceous gland stimulation. In some embodiments, a SARM compound can display androgen receptor (AR) agonist activity with $EC_{50}$ and/or antagonist $IC_{50}$ values generally less than 1 micromolar in one of the known in vitro assays. In some embodiments, tissue selective AR agonism refers to agonism of an AR of a target tissue that is at least about or 2 fold up to more than about or 500 fold, greater than the AR agonism of an AR of a non-target tissue. A non-limiting list of examples of SARMS include 6-(2(R)-(1(S)-hydroxy-2,2,2-trifluoroethyl)-5 (R)-methyl-1-pyrrolidinyl)-4-trifluoromethyl-2(1H)-quinolinone, 4-(2(R)-(1(S)-hydroxy-2,2,2-trifluoroethyl)pyrrolidinyl)-2-trifluoromethyl-benzonitrile, ostarine, analogs of the aforementioned, and compounds having a structure of Formula I:

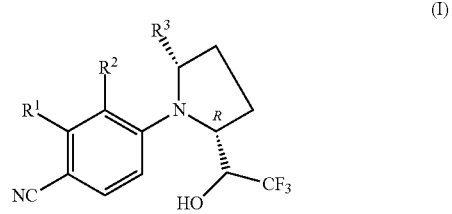

(I)

where $R^1$ can be halogen, pseudohalogen, optionally substituted lower alkyl, optionally substituted haloalkyl or $NO_2$, particularly lower haloalkyl or halogen, and in particular is $CF_3$, F, or Cl; $R^2$ can be hydrogen, halogen, pseudohalogen, optionally substituted lower alkyl or optionally substituted lower haloalkyl, particularly hydrogen or methyl; and $R^3$ can be hydrogen, optionally substituted lower alkyl or optionally substituted lower haloalkyl, particularly hydrogen, or lower alkyl, and in particular hydrogen or methyl.

As used herein, "selective estrogen receptor modulator" or "SERM" is a compound that mimics the action of a natural ER ligand in some tissues but not in others. SERMs are compounds that can elicit estrogen receptor agonism in one or more target tissues (e.g., bone, and/or vagina) and antagonism in other tissues (e.g., breast, CNS, and/or uterus). SERMs can exhibit tissue selective estrogen receptor agonism/antagonism. In some embodiments, SERMs can exhibit antagonistic estrogenic properties in selected tissues (e.g., CNS) to stimulate endogenous androgen production in men without overstimulation of SHBG production in the liver. For example, SERMs can display therapeutic benefits in muscle, bone, and CNS but generally not display adverse effects in prostate, sebaceous glands, and cardiovascular system in men. The tissue selective profile of a SERM compound can be achieved via inherent molecular properties to recruit necessary cofactors in different target tissues to display agonist or antagonist activities, or via selective target tissue distribution through its physical properties or formulation. SERMs can increase biologically active T level in circulation (free-T concentration). In some embodiments, a SERM can have centrally ER antagonistic activity to stimulate endogenous T production in men without over stimulation of SHBG production in the liver and with or without measurable elevation of LH/FSH. In some embodiments, a SERM compound can display ER antagonist activity with $IC_{50}$ and/or agonist activity with $EC_{50}$ values generally less than 1 micromolar for at least one ER subtype in one of the known in vitro assays. Examples of SERM compound include, but are not limited to, lasofoxifene, tamoxifen, raloxifene, clomifene, enclomiphene, toremifene, ormeloxifene, bazedoxifene, ospemifene, fermarelle, afimoxifene, arzoxifene, fulvestrant, and analogs of the aforementioned.

As used herein, "ER modulator" is a compound that mimics the action of a natural ER ligand (for example, estradiol). In some embodiments, an ER modulator can be also a SERM. In some embodiments, an ER modulator can be an ER sub-type selective compound. An ER modulator can be an ER antagonist, an ER agonist or an ER sub-type selective modulator. For example, an ER modular can be an ER antagonist in CNS to stimulate endogenous sex hormone production via a negative gonadal feedback mechanism, an ER agonist in CNS to stimulate endogenous sex hormone production via a positive gonadal feedback mechanism, or an ER sub-type selective modulators to stimulate endogenous sex hormone production. In some embodiments, an ER modulator can display ER antagonist activity with $IC_{50}$ and/or agonist activity with $EC_{50}$ values generally less than 1 micromolar in one of the known in vitro assays. Examples of ER modulators include, but are not limited to, lasofoxifene, tamoxifen, raloxifene, clomifene, enclomiphene, toremifene, ormeloxifene, bazedoxifene, ospemifene, fermarelle, afimoxifene, arzoxifene, fulvestrant, estradiol, 17β-estradiol, estrone, estriol, ethynyl estradiol, mestranol, equine estrogens, synthetic estrogen analogs, GTx-758 and analogs of the aforementioned.

As used herein, "5α-reductase inhibitors" are compounds that can inhibit at least one of the 5α-reductase enzyme subtypes with $IC_{50}$ less than 1 micromolar in a known in vitro assay. Examples of 5α-reductase inhibitors include finasteride, dutasteride, alfatradiol, bexlosteride, episteride, izonsteride, lapisteride, turosteride and analogs of the aforementioned.

As used herein, derivative or analog of a molecule refers to a portion derived from or a modified version of the molecule. In some embodiments, a derivative includes, but is not limited to, acid derivatives, amide derivatives, ester derivatives and ether derivatives. In some embodiments, an analog can be a hydrate, including a hemihydrate, a monohydrate, a dehydrate, and a trihydrate.

As used herein, an "activity" of a SARM or SERM compound provided herein refers to any activity exhibited by a selective AR or ER modulator. Such activities can be tested in vitro and/or in vivo and include, but are not limited to, agonism or antagonism of an androgen or estrogen receptors. Activity can be assessed in vitro or in vivo using recognized assays, for example, by using the co-transfection assay. The results of such assays that indicate that a compound exhibits an activity can be correlated to activity of the compound in vivo, in which in vivo activity can be referred to as biological activity. Assays to determine functionality or activity of androgen or estrogen receptor modulators, including selective androgen or estrogen receptor modulator compounds, are known to those of skill in the art. Exemplary assays include, but are not limited to, fluorescence polarization assay, luciferase assay and co-transfection assay. In certain embodiments, the compounds provided herein are capable of modulating activity of androgen or estrogen receptor in a "co-transfection" assay (also called a "cis-trans" assay), which is known in the art (see e.g., Evans et al., Science 240:889-895 (1988); U.S. Pat. Nos. 4,981,784 and 5,071,773; and Pathirana et al., "Nonsteroidal Human Progesterone Receptor Modulators from the Marie Alga Cymopolia Barbata," *Mol. Pharm.* 47:630-35 (1995)).

As used herein, the term "target activity" refers to a target activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition. As used herein, "biological activity" refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities can be observed in in vitro systems designed to test or use such activities. Thus, for purposes herein a biological activity of a SARM encompasses the agonism or antagonism of an AR.

As used herein, the term "receptor mediated activity" refers to any biological activity that results, either directly or indirectly, from binding of a ligand to a receptor.

As used herein, "androgenic activity" refers to AR agonist activity in androgenic target tissues, such as prostate and seminal vesicles. Androgenic activity is typically demonstrated by increases in the weights of the prostate and seminal vesicles, and facial hair growth, which are accepted in the art as indicators of androgenic activity (e.g., see Lemus et al., J Steroid Biochem Mol Biol 60(1-2): 121-129 (1997)).

As used herein, "anabolic activity" refers to increasing the mass and/or strength of a tissue, such as a connective tissue. Increases in the weight of the levator ani muscle are indicative of anabolic activity, and are accepted in the art as a reliable index of anabolic activity (e.g., see Antonio et al., J Appl Physiol 87: 2016-2019 (1999)). Anabolic activity in bone and muscle decreases bone fracture rates in a subject. Anabolic activity of the compounds provided herein on muscle can be tested by assessing expression of MHC subtypes in skeletal muscle (e.g., see Wright et al., J Appl Physiol. 83(4): 1389-96 (1997)). Bone formation rate, another indication of anabolic activity, can be assessed by osteocalcin level measurement. Plasma osteocalcin levels can be determined using any method known in the art (e.g., see Koyama et al., J Immunol Methods 139(1): 17-23 (1991)). A rat osteocalcin EIA kit is commercially available from Biomedical Technologies Inc. (Stoughton, Mass.).

As used herein, the term "assess" and grammatical variations thereof, is intended to include quantitative and qualitative determination in the sense of obtaining an absolute value for the activity of a compound, and also of obtaining an index, ratio, percentage, visual or other value indicative of the level of the activity. Assessment can be direct or indirect.

As used herein, the term "mediate" means affect or influence. Thus, for example, conditions mediated by an AR are those in which an AR plays a role. AR are known to play a role in conditions including, for example, acne, aging skin, male-pattern baldness, sexual dysfunction, impotence, depression, wasting diseases, HIV-wasting, frailty, cognitive decline, Alzheimer's disease, sleep apnea, hirsutism, hypogonadism, premature ovarian failure, inflammatory arthritis and joint repair, osteopenia, osteoporosis, glucocorticoid-induced osteoporosis, bone fracture, bone damage following bone reconstructive surgery, atherosclerosis, hypercholesterolemia, hyperlipidemia, aplastic anemia and other hematopoietic disorders, obesity, abdominal adiposity, metabolic syndrome, type II diabetes, muscular dystrophies, periodontal disease, sarcopenia, postmenopausal symptoms in women, prostatic hyperplasia, prostate cancer, BPH, cancer cachexia, and hormone-dependent cancers.

As used herein, "$IC_{50}$," refers to an amount, concentration or dosage of a particular test compound that achieves a 50% inhibition of a maximal response, such as modulation of AR activity, in an assay that measures such response. For example, $IC_{50}$ values can be determined using the log-logit (Hill) method.

As used herein, "$EC_{50}$" refers to a dosage, concentration or amount of a particular test compound that elicits a dose-dependent response at 50% of maximal expression of a particular response that is induced, provoked or potentiated by the particular test compound.

As used herein, the term "agonist" refers to a compound, the presence of which results in an activity of a receptor that is the same as the activity resulting from the presence of a naturally occurring ligand for the receptor. An agonist of the AR can bind to the AR and initiate a physiological or a pharmacological response characteristic of that receptor. A "full agonist" induces full activation of the AR population at a given concentration.

As used herein, the term "partial agonist" refers to a compound the presence of which results in a biological activity of a receptor that is of the same type as that resulting from the presence of a naturally occurring ligand for the receptor, but at a lower magnitude. A "partial agonist" is an agonist that is unable to induce maximal activation of the receptor population, regardless of the amount of compound applied.

As used herein, the term "antagonist" refers to a compound, the presence of which results in a decrease in the magnitude of an activity of a receptor. In some embodiments, the presence of an antagonist results in complete inhibition of an activity of a receptor. In some embodiments, the compound binds to AR and blocks or inhibits the androgen-associated responses normally induced by a natural AR ligand.

As used herein, the term "partial antagonist" refers to a compound the presence of which results in a biological activity of a receptor that is of the same type as that resulting from the presence of a naturally occurring ligand for the receptor, but at a lower magnitude. A "partial antagonist" is an antagonist that is unable to induce maximal activation of the receptor population, regardless of the amount of compound applied.

As used herein, the term "alkyl" refers to straight or branched chain substituted or unsubstituted hydrocarbon groups. An alkyl may have 1 to 40 carbon atoms, 1 to 20 carbon atoms, or 1 to 10 carbon atoms. The expression "lower alkyl" refers to an alkyl group of 1 to 6 carbon atoms. An alkyl group can be a "saturated alkyl," meaning that it does not contain any alkene or alkyne groups. An alkyl can be optionally substituted. An alkyl group can be an "unsaturated alkyl," meaning that it contains at least one alkene or alkyne group. An alkyl group that includes at least one carbon-carbon double bond (C=C) also is referred to by the term "alkenyl." An alkyl group that includes at least one carbon-carbon triple bond (C≡C) is referred to by the term "alkynyl." An alkenyl and an alkynyl can be optionally substituted.

In some embodiments, an alkyl contains 1 to 20 carbon atoms (whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms, although the term "alkyl" also includes instances where no numerical range of carbon atoms is designated). An alkyl can be designated as "$C_1$-$C_4$ alkyl" or by similar designations. By way of example only, "$C_1$-$C_4$ alkyl" indicates an alkyl having one, two, three, or four carbon atoms, i.e., the alkyl is selected from among methyl, ethyl, propyl, iso-propyl, n-butyl, iso-butyl, sec-butyl and t-butyl. Thus "$C_1$-$C_4$" includes $C_1$-$C_2$, $C_1$-$C_3$, $C_2$-$C_3$ and $C_2$-$C_4$ alkyl. Alkyls include, but are not limited to, methyl, ethyl, propyl, isopropyl, butyl, isobutyl, tertiary butyl, pentyl, hexyl, ethenyl, propenyl, butenyl, hexenyl, ethynyl, propynyl, butynyl and hexynyl.

As used herein, the term "haloalkyl" alone or in combination refers to an alkyl in which at least one hydrogen atom is replaced with a halogen atom. In some embodiments, two or more hydrogen atom are replaced with halogen atoms in which the halogen atoms are all the same as one another. In other embodiments, two or more hydrogen atom are replaced with halogen atoms in which halogen atoms that are not all the same as one another. Haloalkyls can be saturated haloalkyls, which do not include any carbon-carbon double bonds or any carbon-carbon triple bonds, haloalkenes, which include one or more carbon-carbon double bonds, and haloalkynes, which include one or more carbon-carbon triple bonds. In some embodiments, haloalkyls can be optionally substituted.

As used herein, "pseudohalogen" refers to compounds that behave substantially similar to halides/halogens. Such compounds can be used in the same manner and treated in the same manner as halides/halogens (X—, in which X is a halogen, such as Cl, F or Br). Pseudohalogens include, but are not limited to, cyanide, cyanate, thiocyanate, selenocyanate, trifluoromethoxy, trifluoromethyl and azide.

As used herein, "cycloalkyl" refers to a saturated mono- or multicyclic ring system where each of the atoms forming the ring(s) is a carbon atom. Cycloalkyls can be formed by three, four, five, six, seven, eight, nine, or more than nine carbon atoms. In some embodiments, the ring system can include 3 to 12 carbon atoms. In some embodiments, the ring system can include 3 to 6 carbon atoms. The term "cycloalkyl" includes ring(s) that contain one or more unsaturated bonds. As used herein, the terms "cycloalkenyl" and "cycloalkynyl" are unsaturated cycloalkyl ring system. A cycloalkenyl can have one or more double bonds and a cycloalkynyl can have one or more triple bonds. Cycloalkyls can be optionally substituted. Examples of cycloalkyls include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane, cycloheptene, indanyl, 1,2-dihydro-naphthyl, 1,4-dihydronaphthyl, indenyl, 1,4-naphthoquinonyl and 1,2,3,4-tetrahydronaphthyl.

As used herein, the term "aryl" refers to a monocyclic, bicyclic or tricyclic aromatic system that contains no ring heteroatoms and having a fully delocalized pi-system throughout all the ring(s). In some embodiments, the term aryl refers to bicyclic radicals in which the two rings are aromatic and bicyclic radicals in which only one ring is aromatic. Examples of aryl include phenyl, naphthyl and anthracyl.

As used herein, the term "optionally substituted," refers to a group in which none, one, or more than one of the hydrogen atoms has been replaced with one or more group(s) individually and independently selected from among alkyl, cycloalkyl, heteroalkyl, aryl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, C-amido, N-thiocarbamyl, N-amido, S-sulfonamido, N-sulfonamido, C-carboxy, O-carboxy, isocyanato, thiocyanato, isothiocyanato, nitro, silyl, trihalomethanesulfonyl, and amino, including mono and di substituted amino groups, and the protected derivatives of amino groups. Such protective derivatives (and protecting groups that can form such protective derivatives) are known to those of skill in the art and can be found in references such as Greene and Wuts (*Protective Groups in Organic Synthesis*, 3$^{rd}$ ed., John Wiley & Sons, New York, N.Y., 1999), which is incorporated herein in its entirety. In embodiments in which two or more hydrogen atoms have been substituted, the substituent groups can together form a ring.

Where the number of any given substituent is not specified (e.g., "haloalkyl"), there may be one or more substituents present. For example, "haloalkyl" can include one or more of the same or different halogens. For example, "haloalkyl" includes each of the substituents $CF_3$, $CHF_2$ and $CH_2F$.

As used herein, "enantiomer" refers to one of a pair of molecular entities that are mirror images of each other and non-superimposable. Enantiomeric excess (ee) can be calculated for a mixture of (R) and (S)-enantiomers. The ee can be defined as the absolute value of the mole fractions of $F_{(R)}$ minus the mole fraction of $F_{(S)}$. The percent ee then is the absolute value of the mole fractions of $F_{(R)}$ minus the mole fraction of $F_{(S)}$ multiplied by 100.

As used herein, the term "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Thus, substantially pure object species (e.g., compound) is the predominant species present (i.e., on a molar basis it is more abundant than any other individual species in the composition). In certain embodiments, a substantially purified fraction is a composition wherein the object species includes at least about 50 percent (on a molar basis) of all species present. In certain embodiments, a substantially pure composition will include more than about or 50%, 60%, 70%, 80%, 85%, 90%, 95%, or 99% of all species present in the composition. In certain embodiments, a substantially pure composition will include more than about or 80%, 85%, 90%, 95%, or 99% of all species present in the composition. Methods for purification of the compounds to produce substantially chemically pure compounds are known to those of skill in the art. A substantially chemically pure compound can, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers can be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms also are intended to be included.

As used herein, the term "disease", "condition", or "disorder" refers to a pathological or abnormal condition in an organism resulting from cause or condition including, but not limited to, infections, acquired conditions, genetic conditions, and characterized by identifiable symptoms. In some embodiments, a disease and/or disorder can be caused by the deficiency of a sex hormone.

As used herein, "patient" or "subject" to be treated includes humans and or non-human animals, including mammals. Mammals include primates, such as humans, chimpanzees, gorillas and monkeys; domesticated animals, such as dogs, horses, cats, pigs, goats, cows; and rodents such as mice, rats, hamsters and gerbils.

As used herein, "animal" includes any animal, such as, but not limited to; primates including humans, gorillas and monkeys; rodents, such as mice and rats; fowl, such as chickens; ruminants, such as goats, cows, deer, sheep; ovine, such as pigs and other animals. Non-human animals exclude humans as the contemplated animal.

As used herein, a "combination" refers to any association between two or among more items. The association can be spatial or refer to the use of the two or more items for a common purpose.

As used herein, a "composition" refers to any mixture of two or more products or compounds (e.g., agents, modulators, inhibitors, regulators, etc.). It can be a solution, a suspension, liquid, powder, a paste, aqueous or non-aqueous formulations or any combination thereof.

As used herein, a "fluid" refers to any composition that can flow. Fluids thus encompass pharmaceutical compositions that are in the form of semi-solids, pastes, solutions, aqueous mixtures, gels, lotions, creams and other such compositions.

As used herein, the term "carrier" refers to a compound that facilitates the incorporation of another compound into cells or tissues. For example, dimethyl sulfoxide (DMSO) is a carrier commonly used for improving incorporation of certain organic compounds into cells or tissues.

As used herein, the term "pharmaceutical composition" refers to a chemical compound or composition capable of inducing a desired therapeutic effect in a subject. In some embodiments, a pharmaceutical composition can include an active agent, which is the agent that induces the desired therapeutic effect. In some embodiments, a pharmaceutical composition can include a prodrug. In some embodiments, a pharmaceutical composition can include one or more inactive ingredients, such as carriers and excipients.

As used herein, a "prodrug" refers to a compound that is converted from a less active form into a corresponding more active form in vivo. In certain embodiments, upon in vivo administration, a prodrug is chemically converted to the biologically, pharmaceutically or therapeutically more active form of the compound. In some embodiments, a prodrug can be enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady, *Medicinal Chemistry A Biochemical Approach*, Oxford University Press, New York, pages 388-392 (1985)). Conventional procedures for the selection and preparation of suitable prodrug derivatives are described, for example, in *Design of Prodrugs*, (ed. H. Bundgaard, Elsevier, 1985), which is hereby incorporated herein by reference in its entirety. A non-limiting example of a prodrug for use herein includes those that promote the solubility of alcohols such as by the procedures described in Mahfous, N. H. et al, J. Pharm. Pharmacol. 53: 841-848 (2001) and Bundgaard, H. et al., J. Med. Chem. 32: 2503-2507 (1989), both of which are incorporated herein by reference in their entirety. Prodrugs include compounds where hydroxy, ester, amine or sulfhydryl groups are bonded to any group that, when administered to a mammalian subject, cleaves to form a free hydroxyl, ester, amino, or sulfhydryl group, respectively. Examples of prodrugs include, but are not limited to, acetate, formate and benzoate derivatives of an alcohol functional group within the compounds provided herein.

As used herein, the term "pharmaceutically acceptable formulation" refers to a formulation of a compound that does not significantly abrogate the biological activity, a pharmacological activity and/or other properties of the compound when the formulated compound is administered to a subject. In some embodiments, a pharmaceutically acceptable formulation does not cause significant irritation to a subject.

As used herein, "pharmaceutically acceptable derivative" refers to derivatives of a compound that does not significantly abrogate the biological activity, a pharmacological activity and/or other properties of the compound when the formulated compound is administered to a subject, and include, but are not limited to, salts, esters, enol ethers, enol esters, acetals, ketals, orthoesters, hemiacetals, hemiketals, acids, bases, solvates, hydrates or prodrugs thereof. Such derivatives can be readily prepared by those of skill in this art using known methods for such derivatization. The compounds produced can be administered to animals or humans without substantial toxic effects and either are pharmaceutically active or are prodrugs.

As used herein, the term "pharmaceutically acceptable salt" is intended to include all salts known and used in the art of pharmaceuticals. Pharmaceutically acceptable salts include, but are not limited to, amine salts, such as but not limited to chloroprocaine, choline, N,N'-dibenzyl-ethylenediamine, ammonia, diethanolamine and other hydroxyalkylamines, ethylenediamine, N-methylglucamine, procaine, N-benzyl-phenethylamine, 1-para-chloro-benzyl-2-pyrrolidin-1'-ylmethyl-benzimidazole, diethylamine and other alkylamines, piperazine and tris(hydroxy-methyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Exemplary pharmaceutically acceptable salts include acetate, lactobionate, benzenesulfonate, laurate, benzoate, malate, bicarbonate, maleate, bisulfate, mandelate, bitartrate, mesylate, borate, methylbromide, methylnitrate, calcium edetate, methylsulfate, camsylate, mucate, carbonate, napsylate, bromide, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate and valerate, which can be used as a dosage form for modifying the solubility or hydrolysis characteristics or can be used in sustained release or prodrug formulations. The preparation of the pharmaceutically acceptable salts described above and other typical pharmaceutically acceptable salts is more fully described by Berg et al., "Pharmaceutical Salts," J. Pharm. Sci. 66: 1-19 (1977).

As used herein, "bioavailability" refers to the rate and extent to which the active substance or therapeutic moiety is absorbed from a pharmaceutical form and becomes available at the site of action or reaches systemic circulation. The "absolute bioavailability" of a given pharmaceutical form is compared to that following intravenous administration, which is by definition 100%. Administration by a route other than intravenous administration generally is less than 100%, due to slow or incomplete absorption, or metabolic destruction. "Good bioavailability" generally is >50% and "poor bioavailability" generally is <20%.

As used herein, "PO" refers to Per Os, meaning by mouth or orally.

As used herein, "arthritic condition" or "arthritis" refers to a disease whose underlying etiology is inflammation of a joint, usually accompanied by pain, such as osteoarthritis and rheumatoid arthritis (Taber's Cyclopedic Medical Dictionary; 14$^{th}$ edition, 1983). The compositions disclosed herein are useful, alone or in combination, to treat or prevent arthritic conditions. Exemplary arthritic conditions include Behcet's disease; bursitis and tendinitis; CPPD deposition disease; carpal tunnel syndrome; Ehlers-Danlos syndrome; fibromyalgia; gout; infectious arthritis; inflammatory bowel disease; juvenile arthritis; lupus erythematosus; Lyme disease; Marfan syndrome; myositis; osteoarthritis; osteogenesis imperfecta; osteonecrosis; polyarteritis; polymyalgia rheumatica; psoriatic arthritis; Raynaud's phenomenon; reflex sympathetic dystrophy syndrome; Reiter's syndrome; rheumatoid arthritis; scleroderma; and Sjogren's syndrome. (Bijlsma et al., Am J Reprod Immunol 28(34): 231-234 (1992); Cutolo et al., Ann. N.Y. Acad. Sci. 966: 131-142 (2002); Cutolo, Rheum Dis Clin North Am 26(4): 881-895 (2000); Jansson et al., Arthritis Rheum 44(9): 2168-2175 (2001); Merck Manual (17$^{th}$ edition, pp. 449-451) and Purdie, Br Med Bull 56(3): 809-823 (2000)).

As used herein, "NSAIDs" refer to non-steroidal anti-inflammatory drugs. These drugs exhibit anti-inflammatory and analgesic effects and are commonly used to reduce inflammation and pain, including by decreasing prostaglandin production. Exemplary NSAIDs include, but are not limited to, aspirin, diclofenac/misoprostol, diclofenac potassium, diclofenac, diflunisal, etodolac, fenoprofen, flurbiprofen, ibuprofen, indomethacin, ketoprofen, meclofenamate, mefanamic acid, meloxicam, nabumetone, naproxen and naproxen sodium, oxaprozin, piroxicam, sodium sulindac and tolmetin.

As used herein, "COX-2 inhibitors" refers to drugs that inhibit only the inducible form of the Cyclooxygenase (COX) enzyme (EC 1.14.99.1), which is referred to as COX-2. These compounds are well known in the art (e.g., see PNAS, 89: 7384 (1992); Arch. Opthalmol. 108: 573 (1990); FEBS Letters 372: 83 (1995); Clin, Orthop. 313: 76 (1995); J. Mol. Endocrinol. 16: 107 (1996); Cancer Res. 57: 1625 (1997); Cell 93: 705 (1998); Intl. J. Mol. Med. 2: 715 (1998) and J. Biol. Chem. 274: 9116 (1999)). Exemplary COX-2 inhibitors include, but are not limited to, celecoxib, rofecoxib and valdecoxib.

As used herein, "DMARDs (Disease-Modifying Anti-Rheumatic Drugs)" refer to drugs that function by acting upon the immune system of a subject to slow or stop the underlying processes that cause certain forms of inflammatory arthritis, including rheumatoid arthritis (RA), ankylosing spondylitis, and psoriatic arthritis. DMARDs have been shown to be effective in the treatment of rheumatoid arthritis, psoriatic arthritis, and ankylosing spondylitis and, for some subjects, these drugs can stop progression of the disease. Exemplary DMARDs include, but are not limited to, adalimumab, leflunomide, auranofin, sodium aurothiomalate, chloroquine, etanercept, infliximab, sulfasalazine, mycophenolate, myochrysine, cyclosporine, cyclophosphamide, azathioprine, chlorambucil, methotrexate, minocycline, penicillamine and hydroxychloroquine.

As used herein, "HMG-CoA reductase inhibitors" refers to inhibitors of 3-hydroxy-3-methylglutaryl-CoA reductase. Exemplary HMG-CoA reductase inhibitors include, but are not limited to, lovastatin (see U.S. Pat. Nos. 4,231,938, 4,294,926 and 4,319,039), simvastatin (see U.S. Pat. Nos. 4,444,784, 4,820,850 and 4,916,239), pravastatin (see U.S. Pat. Nos. 4,346,227, 4,537,859, 4,410,629, 5,030,447 and 5,180,589), fluvastatin (see U.S. Pat. Nos. 5,354,772, 4,911, 165, 4,929,437, 5,189,164, 5,118,853, 5,290,946 and 5,356, 896), atorvastatin (see U.S. Pat. Nos. 5,273,995, 4,681,893, 5,489,691 and 5,342,952) and cerivastatin, also known as rivastatin (see U.S. Pat. No. 5,177,080). The structural formulas of these and additional HMG-CoA reductase inhibitors are described at page 87 of M. Yalpani, "Cholesterol Lowering Drugs," Chemistry & Industry, pp. 85-89 and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds that have HMG-CoA reductase inhibitory activity.

As used herein, the terms "osteoporosis" refer to the condition characterized by reduced bone mass and disruption of bone architecture, resulting in increased bone fragility and increased fracture risk, and decreased calcification or density of bone. Osteoporosis is a thinning of the bones with reduction in bone mass due to depletion of calcium and bone protein. In osteoporotic patients, bone strength is abnormal, with a resulting increase in the risk of fracture. The fracture can be in the form of cracking (as in a hip fracture) or collapsing (as in a compression fracture of the spine). The spine, hips, and wrists are common areas of osteoporosis-induced bone fractures, although fractures also can occur in other skeletal areas. Unchecked osteoporosis can lead to changes in posture, physical abnormality, and decreased mobility. Osteoporosis can be identified by bone mineral density measurements.

As used herein, "osteopenia" refers to decreased calcification or density of bone.

As used herein, a "cathepsin inhibitor" refers to an inhibitor of cysteine protease. Cysteine proteases, such as cathepsins, are linked to a number of disease conditions, including arthritis, bone remodeling, inflammation and tumor metastasis. Cathepsin protease inhibitors can inhibit osteoclastic bone resorption by inhibiting the degradation of collagen fibers and thus are useful in the treatment of bone resorption diseases, such as osteoporosis. Examples of cathepsin inhibitors are described in Deaton, Current Topics in Medicinal Chemistry 5(16): 1639-1675 (2005), in U.S. Pat. Nos. 7,279,478, 7,279,472, 7,112,589 and 7,012,075, and in WO 01/49288 and WO 01/77073.

As used herein, a "proton pump inhibitor" refers to osteoclast vacuolar ATPase inhibitors. The proton ATPase found on the apical membrane of the osteoclast has been reported to play a significant role in the bone resorption process and is a target for the design of inhibitors of bone resorption, thereby useful for the treatment and prevention of osteoporosis and related metabolic diseases (e.g., see Niikura, Drug News Perspect. 19(3): 139-44 (2006), Visentin et al., J Clin Invest 106(2): 309-318 (2000) and Niikura et al., Br J of Pharmacology 142: 558-566 (2004)). Exemplary inhibitors include bafilomycin A1, SB242784, FR167356, FR177995, FR202126, FR133605 and NiK-12192 [4-(5,6-dichloro-1H-indol-2-yl)-3-ethoxy-N-(2,2,6, 6-tetramethyl-piperidin-4-yl)-benzamide] (Petrangolini et al., J Pharmacol Exp Ther 318 (3): 939-946 (2006).

As used herein, "PPARγ activators" refers to activators of the peroxisome proliferator-activated receptor gamma (PPARγ), which are known in the art to inhibit osteoclast-like cell formation and bone resorption (e.g., see Okazaki et al., Endocrinology 140: 5060-5065 (1999)). Exemplary PPARγ activators include the glitazones, such as ciglitazone, darglitazone, englitazone, troglitazone, pioglitazone, rosiglitazone, the thiazolidinediones (see, e.g., Yki-Järvinen, New Eng J Med 351(11): 1106-1118 (2004), netoglitazone, 15 deoxy-$\Delta_{12,14}$-prostaglandin $J_2$ and analogs, derivatives, and pharmaceutically acceptable salts thereof.

As used herein, "muscle wasting" refers to atrophy or loss of muscle tissue, which can result from disease or disuse (lack of exercise). As used herein, muscle wasting also includes loss of muscle tone and neurogenic atrophy. Muscle wasting is characterized by a weakening, shrinking, and loss of muscle tissue, often caused by degradation of the contractile myofibrillar proteins actin and myosin (e.g., see Hasselgren et al., Int'l J of Biochemistry & Cell Biology 37(10): 1932 (225); Lynch et al., Pharmacology & Therapeutics 113, (3): 461-487 (2007)).

As used herein, "chronic muscle wasting" refers to chronic (i.e., persisting over a long period of time) progressive loss of muscle mass and/or to the chronic progressive weakening and degeneration of muscle.

As used herein, "cachexia" refers to weakness and a loss of weight caused by a disease or as a side effect of illness. Cardiac cachexia, which includes muscle protein wasting of both the cardiac and skeletal muscle, is a characteristic of congestive heart failure Cancer cachexia is a syndrome that occurs in patients with solid tumors and hematological malignancies and is manifested by weight loss with massive depletion of both adipose tissue and lean muscle mass.

Cachexia also occurs in AIDS. HIV-associated myopathy and/or muscle weakness/wasting is a relatively common clinical manifestation of AIDS. Individuals with HIV-associated myopathy or muscle weakness or wasting typically experience significant weight loss, generalized or proximal muscle weakness, tenderness, and muscle atrophy.

As used herein, "sarcopenia" refers to a debilitating disease that afflicts the elderly and chronically ill patients and is characterized by loss of muscle mass and function.

As used herein, the term "obesity" refers to the state of being well above one's normal weight. Traditionally, a person is considered to be obese if they are more than 20 percent over their ideal weight. Obesity has been defined by the National Institute of Health (NIH) as a Body to Mass Index (BMI) of 30 or above. Overweight due to obesity is a significant contributor to health problems. It increases the risk of developing a number of diseases including, for example, type 2 diabetes, high blood pressure (hypertension), stroke, heart attack (myocardial infarction), heart failure, certain forms of cancer, such as prostate cancer and colon cancer, gallstones and gallbladder disease (cholecystitis), gout and gout-related arthritis, osteoarthritis (degenerative arthritis) of the knees, hips, and the lower back, sleep apnea and Pickwickian syndrome (obesity, red face, underventilation and drowsiness). As used herein, the term "obesity" includes any one of the above-listed obesity-related conditions and diseases.

As used herein, the term "lipid profile" refers to total cholesterol, low density lipoprotein (LDL), high density lipoprotein (HDL), very low density lipoprotein (VLDL), and triglycerides in a subject. LDL, HDL and VLDL are the three types of lipoproteins found in the blood, and they usually represent the types of cholesterol found in the blood (cholesterol combined with a protein and triglyceride).

As used herein, the term "anemia" refers to the condition of having less than the normal number of red blood cells or less than the normal quantity of hemoglobin in the blood. Because of the decreased number of red blood cells or reduced quantity of hemoglobin, the oxygen-carrying capacity of the blood is decreased. A subject with anemia may feel tired and fatigue easily, appear pale, develop palpitations and become usually short of breath. There are many forms of anemia, including aplastic anemia, Fanconi anemia, hereditary spherocytosis, iron deficiency anemia, osteopetrosis, pernicious anemia, sickle cell disease, thalassemia, myelodysplastic syndrome, and a variety of bone marrow diseases.

As used herein, the term "depression" refers to an illness that involves the body, mood and thoughts, that affects the way a person eats and/or sleeps and the way one feels about oneself and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

As used herein, the term "sexual dysfunction" refers to impairment of the emotional or physical responses associated with sexual activity, including sexual desire disorders, sexual arousal disorders, orgasm disorders, and sexual pain disorders, which can prevent an individual from engaging in sexual activity or result in inadequate sexual functioning. Sexual dysfunction includes lack of sexual desire, anxiety about sexual performance, difficulty in becoming aroused, inability to achieve orgasm (anorgasmia), premature ejaculation, erectile dysfunction, impotence, frigidity, dyspareunia, vaginismus and dyspareunia (e.g., see American Society for Reproductive Medicine, "Sexual Dysfunction—Patient's Fact Sheet" (1998)).

As used herein, the term "male sexual dysfunction" includes impotence, loss of libido, orgasm dysfunction (e.g., premature ejaculation or retrograde ejaculation) and erectile dysfunction.

As used herein, the term "erectile dysfunction" refers to a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

As used herein, the term "female sexual dysfunction" includes dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an SARM compound provided herein can result in improved blood flow, improved lubrication, improved sensation, facilitation of reaching orgasm, reduction in the refractory period between orgasms, and improvements in arousal and desire.

As used herein, the term "libido" refers to sexual desire.

As used herein, the term "hypogonadism" refers to a condition resulting from or characterized by abnormally decreased functional activity of the gonads, with retardation of growth and sexual development.

As used herein, the term "cognition" refers to the process of knowing, specifically the process of being aware, knowing, thinking, learning and judging. As used herein, the term "mood" refers to a temper or state of the mind. As used herein, the term "alteration" or "alterations" refers to any change for the positive or negative, in cognition and/or mood.

As used herein, the term "hair loss" refers to alopecia, or baldness, such as in the common type of male-pattern baldness. Hair loss affects both males and females.

As used herein, "frailty" refers to an adverse, primarily gerontologic, health condition, characterized by low functional reserve, accelerated osteoporosis, easy tiring, decreased muscle strength, high susceptibility to disease and decreased libido (e.g., see Bandeen-Roche et al., The Journals of Gerontology Series A: Biological Sciences and Medical Sciences 61: 262-266 (2006)).

As used herein, "connective tissue" refers to tissue generally of mesodermal origin that is characterized by a highly vascular matrix and which forms the supporting and connecting structures of the body. Connective tissue includes collagenous, elastic, and reticular fibers, muscle, adipose tissue, cartilage, and bone. Exemplary connective tissue includes adipose tissue, areolar tissue, blood, bone (including cancellous bone, compact bone, cortical bone, spongy bone and trabecular bone), bone marrow, cartilage, collagen, cutis, elastic tissue, endoneurium, fascia, ligament, mesenchymal connective tissue, mucous connective tissue, muscle, osseous tissue, perineurium, perimysium, submucosa and tendon.

As used herein, "bone mineral density" or "BMD" refers to the density of minerals (such as calcium) in bone. BMD is determined using a special X-ray, computed tomography (CT) scan, or ultrasound. This information is used to estimate the strength of bones. Increasing mineral content of bone increases the density of the bone and its strength. The denser the bone, the less likely it is to break.

B. METHODS, COMPOSITIONS AND INDICATIONS

Androgen therapy has been used to treat a variety of male disorders such as reproductive disorders and primary or secondary male hypogonadism. A number of natural or synthetic AR agonists have been investigated for the treatment of musculoskeletal disorders, such as bone disease, hematopoietic disorders, neuromuscular disease, rheumatological disease, wasting disease, and for HRT, such as female androgen deficiency. In addition, AR antagonists, such as flutamide and bicalutamide, are used to treat BPH and prostate cancer. 5α-Reductase inhibitors, such as finasteride or dutasteride, are used to treat BPH and male pattern baldness.

Progress of androgen therapy has been limited by the inability to separate desirable anabolic activities from undesirable or dose-limiting side effects. Recent advances in the development of SARMs that exhibit tissue selectivity in targeting the AR while eliminating certain undesired side effects (e.g., see Negro-Vilar, A. JCE&M 54(10):3459-62 (1999); Reid et al., Investigational New Drugs 17: 271-284 (1999)). For example, SARMs and uses thereof have been identified in the art (e.g., see U.S. Pat. Appl. No. US2007254875 and U.S. Pat. Nos. 7,301,026; 7,291,673; 7,288,553; 7,268,232; 7,268,153; 7,253,210; 7,217,720; 7,214,804; 7,214,693; 7,214,690; 7,205,437; 7,186,838; 7,026,500; 7,022,870; 6,998,500; 6,995,284; 6,960,474; 6,899,888; 6,838,484; 6,569,896 and 6,492,554; Thevis et al., Rapid Commun Mass Spectrom. 21(21): 3477-3486 (2007); Kilbourne et al., Curr Opin Investig Drugs. 8(10): 821-829 (2007); Higuchi et al., Bioorg Med Chem Lett. 17(19): 5442-5446 (2007); Zhang et al., J Med Chem. 50(16): 3857-3869 (2007); Gao et al; Drug Discov Today. 12(5-6): 241-248 (2007); Omwancha et al., Curr Opin Investig Drugs. 7(10): 873-881 (2006); Kazmin et al., Mol Endocrinol. 20(6): 1201-1217 (2006); Segal et al., Expert Opin Investig Drugs. 15(4): 377-387 (2006); Cadilla et al., Curr Top Med Chem. 6(3): 245-270 (2006); Chen et al., Mol Interv. 5(3): 173-188 (2005); Buijsman et al., Curr Med Chem. 12(9): 1017-1075 (2005); Brown et al., Endocrinology 145(12): 5417-5419 (2004); Chen et al., J Pharmacol Exp Ther. 312(2): 546-553 (2005); Marhefka et al; J Med Chem. 47(4): 993-998 (2004); and Yin et al., J Pharmacol Exp Ther. 304(3): 1334-1340 (2003)).

SARMs can demonstrate better pharmacokinetic and specificity profiles than other steroidal androgen therapies. In particular, non-steroidal SARMs display therapeutic benefit but do not display the androgenic effects associated with other androgen therapies. These adverse androgenic effects include manifestations such as prostate enlargement, acne, hirsutism, virilization and masculinization. Androgen therapies and the SARMs can suppress endogenous androgen production through the gonadal feedback mechanism, which may be related to the negative effect on lipid profile and potential risks in cardiovascular system. The complex relationship of androgens with cardiovascular system raises many concerns of long-term use of the androgen or SARM therapies, especially in elderly.

Methods and compositions provided herein can offer additional benefit/risk ratio relative to SARMs, especially mitigating the risks in cardiovascular system. For example, a method and/or composition described herein can exhibit beneficial activity on target tissues without increasing the risks in certain other tissues of concern (e.g., mitigating the potential risks in cardiovascular system by stimulating or avoiding suppression of endogenous sex hormone production).

A SERM compound can stimulate endogenous T production with neutral or beneficial effects on lipid profile and cardiovascular system. The increased endogenous T has beneficial effects on muscle, bone, and CNS. 5α-reductase inhibitors tissue-selectively can suppress conversion of T into biologically more active DHT in prostate and sebaceous glands to reduce the risks in those tissues. The SERM compounds also can offer an additional benefit in bone via ER mediated mechanisms.

A SARM compounds can exhibit anabolic activity in muscle, bone, and CNS with reduced activity in prostate and sebaceous glands. SARMs related negative lipid changes and the suppression effect on endogenous sex hormone production can be countered by an ER modulating compound (e.g., SERMs, estrogens, or ER sub-type selective modulators) via the gonadal feedback mechanisms. In some embodiments, a method and/or compositions described herein can have neutral or beneficial effects on the cardiovascular system. For uses in female subjects, certain ER modulating compounds, such as SERMs, can offer additional benefits in bone, breast, uterus, and vagina through ER mediated mechanisms.

Topical T replacement therapies have been used to treat hypogonadism in men. An SERM compound, enclomiphene, has been in development for male hypogonadism by stimulating endogenous T production. Lasofoxifene has a biological profile that is different from other SERMs and demonstrated a unique pharmacokinetic/pharmacodynamic profile in men with superior potency and prolonged mechanism of action in stimulation of T production. In some embodiments, a method described herein generally relates to the use of an effective amount of lasofoxifene for the treatment of hypogonadism in men without a potential negative effect on the cardiovascular system that exists in direct androgen therapies.

Methods and compositions provided herein can display micromolar or submicro-molar binding affinity for their corresponding receptors or enzymes. The SERM, SARM, and ER modulating compounds can demonstrate target receptor agonist or antagonist activity, as evidenced by their activity in standard in vitro assays, such as the co-transfection assay described herein. For example, the SERM, SARM, and ER modulating compounds can demonstrate a potency ($IC_{50}$ or $EC_{50}$) of 1 μM or less in the co-transfection assay described herein. In some embodiments, the SERM, SARM, and ER modulating compounds can demonstrate a potency ($IC_{50}$ or $EC_{50}$) of 100 nM or less in the co-transfection assay described herein. In some embodiments, the SERM, SARM, and ER modulating compounds can demonstrate a potency ($IC_{50}$ or $EC_{50}$) of 50 nM or less in the co-transfection assay described herein. In some embodiments, the SERM, SARM, and ER modulating compounds can demonstrate a potency ($IC_{50}$ or $EC_{50}$) of 10 nM or less in the co-transfection assay described herein. The 5α-reductase inhibitors can demonstrate a potency ($IC_{50}$) of 1 μM or less in at least one of the enzyme subtypes in one of the known in vitro assays. In some embodiments, a method and/or composition described herein can be useful in treating mammals suffering from disorders mainly related to AR function. Methods and compositions described herein can be used to treat disorders related to mainly AR function, such as, androgen deficiency, disorders that can be ameliorated by endogenous androgen production or androgen replacement, or that can be improved by endogenous androgen production or androgen replacement.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used for the prevention, treatment, or amelioration of one or more of the symptoms of diseases or disorders associated with AR activity. Diseases and disorders that can be treated include those caused by androgen deficiency and/or those that can be ameliorated by androgen administration or stimulation of endogenous androgen production.

Disorders, diseases or conditions that are caused by androgen deficiency or hypoactivity or subsensitivity of AR, or that can be ameliorated by androgen replacement or stimulation of endogenous androgen production and can be treated, ameliorated and/or prevented by a method and/or composition described (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) include, but are not limited to, aging skin; Alzheimer's disease; anemias, such as for example, aplastic anemia; anorexia; arthritis, including inflammatory arthritis, rheumatoid arthritis, osteoarthritis and gout; arteriosclerosis; atherosclerosis; bone disease, including metastatic bone disease; bone damage or fracture, such as by accelerating bone fracture repair and/or stimulation of osteoblasts and/or stimulation of bone remodeling and/or stimulation of cartilage growth; distraction osteogenesis; reduced bone mass, density or growth; bone weakening induced by glucocorticoid administration; musculoskeletal impairment (e.g., in the elderly); cachexia; cancer, including breast cancer and osteosarcoma; cardiac dysfunction (e.g., associated with valvular disease, myocardial infarction, cardiac hypertrophy or congestive heart failure); cardiomyopathy; catabolic side effects of glucocorticoids; Crohn's disease; growth retardation in connection with Crohn's disease; short bowel syndrome; irritable bowel syndrome; inflammatory bowel disease; ulcerative colitis; cognitive decline and impairment; dementia; short term memory loss; COPD; chronic bronchitis; decreased pulmonary function; emphysema; decreased libido in both men and women; depression; nervousness, irritability and/or stress; reduced mental energy and low self-esteem (e.g., motivation/assertiveness); dyslipidemia; erectile dysfunction; frailty; age-related functional decline ("ARFD") in the elderly; growth hormone deficiency; hematopoietic disorders; sex hormone deficiency (male and female); hyper-cholesterolemia; hyperinsulinemia; hyperlipidemia; hypertension; hyperandrogenemia; hypogonadism (including primary and secondary); hypothermia (including hypothermia following anesthesia); impotence; insulin resistance; type 2 diabetes; lipodystrophy (including in subjects taking HIV or AIDS therapies such as protease inhibitors); male menopause; metabolic syndrome (syndrome X); loss of muscle strength and/or function (e.g., in the elderly); muscular dystrophies; muscle loss following surgery (e.g., post-surgical rehabilitation); muscular atrophy (e.g., due to physical inactivity, bed rest or reduced weight-bearing conditions such as microgravity); neurodegenerative diseases; neuromuscular disease; decreased platelet count; platelet aggregation disorders; obesity; osteoporosis; osteopenia; glucocorticoid-induced osteoporosis; osteochondro-dysplasias; periodontal disease; premenstrual syndrome; postmenopausal symptoms in women; Reaven's syndrome; rheumatological disease; sarcopenia; male and female sexual dysfunction (e.g., erectile dysfunction, decreased sex drive, sexual well-being, decreased libido); physiological short stature, including growth hormone deficient children and short stature associated with chronic illness and growth retardation associated with obesity; tooth damage (such as by acceleration of tooth repair or growth); thrombocytopenia; vaginal dryness; atrophic vaginitis; ventricular dysfunction; wasting, including wasting secondary to fractures and wasting in connection with COPD, chronic liver disease, AIDS, weightlessness, cancer cachexia, burn and trauma recovery, chronic catabolic state (e.g., coma), eating disorders (e.g., anorexia), chemotherapy, multiple sclerosis or other neurodegenerative disorders.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to stimulate pulsatile growth hormone release; to improve bone strength, muscle strength and tone; to reduce subcutaneous fat in a subject; to enhance bone and muscle performance/ strength; to increase athletic performance; to attenuate or reverse protein catabolic responses following trauma (e.g., reversal of the catabolic state associated with surgery, congestive heart failure, cardiac myopathy, burns, cancer, COPD); to improve sleep quality and/or correct the relative hyposomatotropism of senescence due to high increase in REM sleep and a decrease in REM latency; to treat age related decreased testosterone levels in men; to optimizing lipid profile; and for hormone replacement therapy, such as female androgen deficiency and male androgen decline.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can act as antagonists in specific tissues, and thus also are useful in treating conditions where elevated androgen concentration or activity causes symptoms. In some embodiments, methods and/or compositions provided herein can be used to treat conditions whose etiology involves hyperactivity of AR or that are responsive to treatment with a moderate AR antagonist. Such conditions, include, but are not limited to, *acanthosis nigricans*, acne, adrenal hyperandrogenism, androgenetic alopecia (male-pattern baldness), BPH, cancer (e.g., cancer of the breast, bladder, brain, endometrium, lung (non-small cell lung cancer), pancreas, kidney, ovaries, lymphatic system, and skin); bulimia nervosa; chronic fatigue syndrome (CFS); chronic myalgia; acute fatigue syndrome; counteracting preeclampsia, eclampsia of pregnancy and preterm labor; delayed wound healing; erythrocytosis; gestational diabetes; hirsutism; hyper-insulinemia including nesidioblastosis; hyperandrogenism; hypercortisolism; Cushing's syndrome; hyperpilosity; menstrual irregularity; polycystic ovarian syndrome; seborrhea; sleep disorders; sleep apnea; and visceral adiposity.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can have an agonistic activity on muscle and bone tissue, and have a neutral or antagonistic effect on prostate tissue. In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to treat or prevent a condition selected from among muscle wasting, cachexia, frailty, sarcopenia, osteopenia, osteoporosis, hypogonadism and sexual dysfunction.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can target anabolic tissue, such as connective tissue, including bone and muscle, and can be used to increase the mass of a connective tissue in a subject and to reverse connective tissue loss in a subject with reduced risks in other tissues such as prostate, uterus, breast, sebaceous glands, and cardiovascular system.

The methods described herein can be practiced by administering to a subject a combination therapy described herein (an effective amount of a selective estrogen receptor modulator and an effective amount of a 5α-reductase inhibitor, or a pharmaceutically acceptable salt, ester or prodrug of the foregoing, and/or an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing). In some embodiments, the condition can be responsive to AR modulation in a subject. In some embodiments, the disease or condition can be responsive to an AR agonist. In other embodiments, the disease or condition can be responsive to an AR antagonist. Embodiments described herein can further include identifying a subject in need of such treatment and administering to the subject a combination of compounds described herein.

1. Muscle Wasting

Muscle wasting is associated with chronic, neurological, genetic or infectious pathologies, diseases, illnesses or conditions. In some embodiments, the pathology, illness, disease or condition is chronic. In some embodiments, the pathology, illness, disease or condition is genetic. In some embodiments, the pathology, illness, disease or condition is neurological. In some embodiments, the pathology, illness, disease or condition is infectious. As described herein, the pathologies, diseases, conditions or disorders for which the compositions provided herein are administered are those that directly or indirectly produce a loss of muscle mass, or that result in a muscle wasting disorder.

Muscle wasting infectious pathologies, diseases, illnesses or conditions include AIDS; burns; cachexias, such as AIDS cachexia, cancer cachexia, and cardiac cachexia; cancer; cardiomyopathy; chronic kidney or heart failure; COPD; denervation; diabetes; emphysema; end stage renal failure; frailty; HIV infection; inactivity; leprosy; malnutrition; muscle atrophies such as Post-Polio Muscle Atrophy (PPMA) or X-linked spinal-bulbar muscular atrophy (SBMA); muscular dystrophies, such as Duchemie Muscular Dystrophy, myotonic dystrophy, Becker's muscular dystrophy (benign pseudohypertrophic muscular dystrophy), limb-girdle muscular dystrophy, facioscapulohumeral muscular dystrophy (FSHD), congenital muscular dystrophy, Oculopharyngeal Muscular Dystrophy (OPMD), distal muscular dystrophy and Emery-Dreifuss muscular dystrophy; osteomalacia; renal disease; sarcopenia; sepsis; and tuberculosis. In addition, other circumstances and conditions are linked to and can cause muscle wasting. These include chronic lower back pain, advanced age, CNS injury, peripheral nerve injury, spinal cord injury, chemical injury, CNS damage, microgravity, peripheral nerve damage, spinal cord damage, chemical damage, burns, disuse, deconditioning that occurs when a limb is immobilized, long term hospitalization due to illness or injury, and alcoholism. Muscle wasting, if left unabated, can have dire health consequences. For example, the changes that occur during muscle wasting can lead to a weakened physical state that is detrimental to an individual's health, resulting in increased susceptibility to infraction and poor performance status. In addition, muscle wasting is a strong predictor of morbidity and mortality in patients suffering from cachexia and AIDS.

Muscle wasting due to infectious pathologies includes muscle wasting disorders due to infection with coxsackie virus, enterovirus, Epstein-Barr virus, herpes zoster, HIV, influenza, mycobacteria, *rickettsia, schistosoma, trichinella* or trypanosomes.

The loss of muscle mass that occurs during muscle wasting can be characterized by a breakdown or degradation of muscle protein, such as by muscle protein catabolism. Protein catabolism occurs because of an unusually high rate of protein degradation, an unusually low rate of protein synthesis, or a combination of both. Protein catabolism or depletion, whether caused by a high degree of protein degradation or a low degree of protein synthesis, leads to a decrease in muscle mass and to muscle wasting.

Muscle wasting also is associated with advanced age. It is believed that general weakness in old age is due to muscle wasting. As the body ages, an increasing proportion of skeletal muscle is replaced by fibrous tissue. The result is a significant reduction in muscle power, performance and endurance. Long term hospitalization due to illness or injury, or muscle disuse that occurs, for example, when a limb is immobilized, also can lead to muscle wasting. Patients suffering injuries, chronic illnesses, burns, trauma or cancer, who are hospitalized for long periods of time, often exhibit a long-lasting unilateral muscle wasting.

Administration of anabolic steroids have demonstrated the ability to increase weight and muscle mass in some patients with muscle wasting, such as in cancer patients. However, administration of anabolic steroids can result in unwanted androgenic side effects, including development of oily skin or acne, as well as masculinization in women and prostate stimulation in men, and negative effects on lipid profile and cardiovascular system. SARMs have demonstrated efficacy for attenuating muscle wasting across a range of disorders (e.g., see Allen et al. Endocrine 32(1): 41-51 (2007); Lynch et al., Pharmacology & Therapeutics 113(3): 461-487 (2007); Gao et al., Endocrinology 146(11): 4887-4897 (2005); Lynch, Expert Opinion on Emerging Drugs 9(2): 345-361 (2004); U.S. Pat. Appl. Pub. No. 20060111441 and WO03049675). SARMs generally demonstrate predominately anabolic activity in muscle and bone with minimal androgenic effects in most other tissues but do not address the complication in lipid profile and cardiovascular system. In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be useful for treating muscle wasting. In some embodiments, muscle wasting can be caused by a condition selected from among andropause, spinal muscular atrophies, muscular dystrophies (e.g., Duchenne, Myotonic and Becker), myasthenia gravis, cachexias such as AIDS cachexia, cardiac cachexia, and cancer cachexia, cancer, COPD, emphysema, diabetes, HIV infection, AIDS, sepsis, tuberculosis, renal failure, heart failure, cardiomyopathy, bed rest, disuse, inactivity, microgravity, malnutrition, sarcopenia, aging and frailty. In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can useful for treating sarcopenia.

2. Muscle Tone and Strength

AR agonists are known to have a beneficial effect on muscle tone and strength (e.g., see Gao et al., Endocrinology 146(11): 4887-4897 (2005), Jasuja et al, J Clin Endocrinol Metab. 90(2): 855-863 (2005) and Ferrando et al, Am J Physiol Endocrinol Metab. 282(3): E601-E607 (2002). Androgen replacement in healthy, hypogonadal men results in gains in fat-free mass, muscle size and maximal voluntary strength (e.g., see Bhasin et al., J. Endocrin. 170: 27-38 (2001)). Thus, in some embodiments, a method and/or composition described herein can stimulate muscle growth and can be used for treatment of sarcopenia and frailty with increased benefit/risk ratio in cardiovascular system comparing to SARMs. In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can useful for increasing muscle tone and/or strength.

3. Osteoporosis

Osteoporosis is a disease characterized by low bone mass and structural deterioration of bone tissue leading to bone fragility and an increased susceptibility to fractures of the hip, spine, ribs and wrist. Loss of estrogens or androgens causes an imbalance between resorption and formation of bone by prolonging the lifespan of osteoclasts and shortening the lifespan of osteoblasts. Loss of androgens also may induce bone loss by increasing the rate of bone remodeling (Lindberg et al., Minerva Endocrinol. 30(1): 15-25 (2005)). The beneficial effects of androgens on bone in postmenopausal osteoporosis are described in art (e.g., see Hofbauer et al., Eur. J. Endocrinol. 140: 271 286 (1999). Androgens also play an important role in bone metabolism in men (e.g., see Anderson et al., Bone 18: 171-177 (1996). Androgen receptor modulator compounds also have been shown to improve bone strength in a rat model of post-menopausal osteoporosis (e.g., see Martinborough et al., J Med Chem. 50(21): 5049-5052 (2007)). Estrogens and SERMs have been demonstrated significant clinical benefits in prevention and treatment menopausal related osteoporosis (e.g., see U.S. Pat. Nos. 4,729,999, 4,894,373 and 5,393,763). In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can activate the function of both androgen and estrogen receptors in bone and provide benefits superior than that of androgen or estrogen receptor without the combination of compounds. In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can useful for the treatment of a condition or disorder selected from among osteoporosis, osteopenia, glucocorticoid-induced osteoporosis and bone fracture in women and/or men.

4. Prostate Disease

In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can be used for the treatment of a prostate disease, such as benign prostatic hyperplasia (BPH). In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can block or inhibit (antagonize) the function of the AR in the prostate of a male individual or reduce the testosterone effect in the prostate by blocking the conversion to DHT.

5. Hematopoietic Conditions and Disorders

Hematopoiesis is a constant process in which specialized blood cells, such as erythrocytes, B and T lymphocytes, platelets, granulocytes, monocytes, and macrophages, are generated from hematopoietic stem cells. A number of undesired hematopoietic conditions can occur in a subject. These include inadequate production of, or increased destruction of, platelets, red blood cells or white blood cells. For example, inadequate platelet or blood cell production or destruction can result in aplastic anemia, refractory anemias, idiopathic thrombocytopenia purpura, immune thrombocytopenias, leukemia, myelodysplastic and preleukemia syndromes, megaloblastic anemia and platelet deficiency, myeloproliferative disorders and uremia. Hematopoietic cytokines, such as erythropoietin, have been used to treat various diseases arising from imbalances between degradation and reconstitution of blood cells or from generation of inappropriate numbers of certain blood cells.

Androgens are known in the art to stimulate renal hypertrophy and erythropoietin (EPO) production. Androgens have been used to treat anemia caused by chronic renal failure. In addition, androgens increase serum EPO levels in anemic patients with non-severe aplastic anemia and myelodysplastic syndromes. Thus, in some embodiments, a method and/or composition provided herein can be used to treat certain hematopoietic disorders including aplastic anemia, refractory anemias, idiopathic thrombocytopenia purpura, immune thrombocytopenias, leukemia, preleukemia/myelodysplastic syndromes, megaloblastic anemia and platelet deficiency, myeloproliferative disorders and uremia. In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be useful for treating a hematopoietic condition.

6. Neurodegenerative Diseases and Disorders

In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used in the treatment of neurodegenerative diseases, such as Alzheimer's disease. The art teaches that androgens and SARMs can be useful in preventing the onset or delaying the progression of Alzheimer's disease in male patients (e.g., see Fuller et al., J Alzheimer's Dis. 12(2): 129-142 (2007). It is known in the art that AR agonists have therapeutic value in the treatment of neurodegenerative diseases such as Alzheimer's disease (e.g., see Hammond et al., J. Neurochem. 77: 1319-1326 (2001)). AR agonists, such as T, have been shown to reduce secretion of β-amyloid peptides characteristic of Alzheimer's disease and can therefore be used in the treatment of Alzheimer's disease (Gouras et al., Proc. Nat. Acad. Sci. USA 97: 1202-1205 (2000)). AR agonists also have been shown to inhibit hyperphosphorylation of proteins implicated in the progression Alzheimer's disease (e.g., see Papasozomenos, Proc. Nat. Acad. Sci. USA 99: 1140-1145 (2002)). Studies have shown that apoE4 contributes to cognitive decline in Alzheimer's disease by reducing AR levels in the brain, and that stimulating AR-dependent pathways can reverse apoE4-induced cognitive deficits (e.g., see Raber et al., J Neurosci. 22(12): 5204-5209 (2002). Thus, in some embodiments, a method and/or composition provided herein are useful in the treatment of Alzheimer's disease and other neurodegenerative disorders. Additionally, AR modulators can be useful in treating cognitive impairment (see Pfankuch et al., Brain Res. 1053(1-2): 88-96 (2005) and Wisniewski, Horm. Res. 58: 150-155 (2002)). Studies have shown that age-related decline in testosterone levels is associated with depression and that testosterone has been useful in the treatment of depression (e.g., see Carnahan et al., Drugs Aging 21(6): 361-376 (2004). Accordingly, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be useful in the treatment of cognitive impairment and/or depression.

7. Obesity

Obesity has been associated with alterations in androgen secretion, transport, metabolism, and action, with obese men displaying a decrease of T levels with increasing body weight and obese women, especially those with abdominal obesity, displaying a condition of functional hyperandrogenism (e.g., see Pasquali, Fertil Steril. 85(5): 1319-1340 (2006). It has been demonstrated in the art that androgen administration reduces subcutaneous and visceral fat in obese patients (e.g., see Lovejoy et al., Int. J. Obesity 19: 614-624 (1995) and Lovejoy et al., J. Clin. Endocrinol. Metab. 81: 2198-2203 (1996)). Therefore, in some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be beneficial in the treatment of obesity. In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to treat abdominal adiposity (e.g., in a male subject).

8. Insulin Disorders and Diabetes

In vivo studies have shown that the AR plays a key role in the development of insulin resistance, which may contribute to the development of type 2 diabetes and cardiovascular disease (e.g., see Lin et al., Diabetes 54(6): 1717-1725 (2005). AR agonists also can have therapeutic value against metabolic syndrome (insulin resistance syndrome, syndrome X), particularly in men. Low levels of total and free T in men have been associated with type 2 diabetes, visceral obesity, insulin resistance (hyperinsulinemia, dyslipidemia) and metabolic syndrome (e.g., see Laaksonen et al., Diabetes Care 27(5): 1036-1041 (2004), Marin et al., *Obesity Res*. 1(4): 245-251 (1993) and Laaksonen et al., Euro. J Endocrin 149: 601-608 (2003)) and, in women, there is a correlation between high androgen levels and insulin resistance (e.g., see Corbould, J Endocrinol. 192(3): 585-594 (2007). Accordingly, in some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to treat insulin resistance and/or type II diabetes.

9. Sexual Dysfunction

T is used as a treatment for sexual dysfunction in hypogonadal patients (Yassin et al., World Journal of Urology 24:6: 639 (2006). It is known in the art that androgen deficiency in women is clinically often associated with a loss of libido and energy (e.g., Arlt, Eur J Endocrinol 154(1): 1-11 (2006) and Rivera-Woll et al., Human Reproduction Update 10(5): 421 (2004)). Low androgen levels have been shown to contribute to the decline in sexual interest in many women during their later reproductive years (Davis, Clin. Endocrinol. Metab. 84: 1886-1891 (1999)). In clinical trials, women treated with the androgen DHEA exhibited an increase in the frequency of sexual thoughts, interest, and satisfaction compared to women taking a placebo (e.g., see Arlt et al., N Engl. J. Med. 341:1013-1020 (1999) and Miller, *J. Clin. Endocrinol. Metab.* 86: 2395-2401 (2001)). Androgen deficiency in men is related to diminished libido (e.g., see Fine, JAOA Supplement 1 Vol 104(1): S9-S15 (2004)). It also is known in the art that erectile response is centrally and peripherally regulated by androgens. Studies have shown that treatment with T positively impacts the tissues of the penis involved in the mechanism of erection, and that T deficiency impairs the anatomical and physiological erectile capacity, which is reversible upon androgen replacement (e.g., see Gooren et al., Asian Journal of Andrology 8(1): 3-9 (2006). In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be useful in the treatment of sexual dysfunction, for example, the aforementioned methods and/or compositions can be useful as hormone replacement therapy in hypogonadic (androgen deficient) men.

In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can be useful in activating the function of the AR in bone and/or muscle tissue and blocking or inhibiting the function of the AR in the prostate of a male individual or in the uterus of a female individual with neutral or beneficial effects on cardiovascular system.

10. Arthritic Conditions and Inflammatory Disorders

AR modulators are known in the art to be useful in the treatment of arthritic conditions or inflammatory disorders (e.g., see Cutolo et al., Ann. N.Y. Acad. Sci. 966: 131-142 (2002); Cutolo, Rheum Dis Clin North Am 26(4): 881-895 (2000); Bijlsma et al., Am J Reprod Immunol 28(34): 231-234 (1992); Jansson et al., Arthritis Rheum 44(9): 2168-2175 (2001); and Purdie, Br Med Bull 56(3): 809-823 (2000). Also, see Merck Manual, 17th edition, pp. 449-451.)

In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to treat or prevent arthritic conditions, such as Behcet's disease, bursitis, tendonitis, CPPD deposition disease, carpal tunnel syndrome, Ehlers-Danlos syndrome, fibromyalgia, gout, infectious arthritis, inflammatory bowel disease, juvenile arthritis, lupus erythematosus, Lyme disease, Marfan syndrome, myositis, osteoarthritis, osteogenesis imperfecta, osteonecrosis, polyarteritis, polymyalgia rheumatica, psoriatic arthritis, Raynaud's phenomenon, reflex sympathetic dystrophy syndrome, Reiter's syndrome, rheumatoid arthritis, scleroderma and Sjogren's syndrome. In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to treat or prevent an inflammatory disorder.

11. Modifying Lipid Profile

In some embodiments, a method and/or composition provided herein can be capable having a beneficial lipid profile mediated through the ER modulating component of the combination therapies. In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to reduce total cholesterol, LDL, VLDL, and/or triglycerides. In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to improve the LDL/HDL ratio by increase HDL and/or decrease LDL.

12. Postmenopausal Conditions

Reduced levels of T in postmenopausal women are associated with loss of libido, decreased sexual activity, diminished feelings of physical well-being and fatigue (e.g., see Kingsberg, J Sex Med. 4 Suppl 3: 227-234 (2007). In some embodiments, a method and/or composition provided herein disclosed herein can exhibit AR agonism in CNS and can be used to treat vasomotor symptoms, such as hot flashes, and other postmenopausal conditions, and to increase energy. There is evidence in the art that hot flashes decrease in women treated with androgens (e.g., see Notelovitz, Mayo Clin Proc. 79(4 Suppl): S8-S13 (2004)). Certain ER modulating compounds have demonstrated to improve the postmenopausal conditions. In some embodiments, a method and/or a composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can be used to treat a postmenopausal condition in a female subject. In some embodiments, the postmenopausal condition can be selected from among hot flashes, loss of libido, decreased feelings of wellbeing and fatigue.

Methods of use are provided herein. The methods include clinical uses for altering AR/ER activities and for treatment, prevention, or amelioration of one or more symptoms of diseases or disorder that are modulated by mainly AR and/or ER activity, or in which AR and/or ER activity is primarily implicated.

Some embodiments disclosed herein relate generally to a method of treating a disease, disorder or condition that can include administering an effective amount of a selective estrogen receptor modulator and an effective amount of a 5α-reductase inhibitor, or a pharmaceutically acceptable salt, ester or prodrug of the foregoing. Some embodiments disclosed herein relate generally to a method of modulating an androgen receptor and/or an estrogen receptor that can include contacting the androgen receptor or estrogen receptor with an effective amount of a selective estrogen receptor modulator and contacting the steroid 5α-reductase with an effective amount of a 5α-reductase inhibitor, or a pharmaceutically acceptable salt, ester or prodrug of the foregoing, wherein the activity of the androgen receptor and/or the activity of the estrogen receptor is modulated.

In some embodiments, the SERM can be an estrogen receptor agonist. In other embodiments, the SERM can be an estrogen receptor partial agonist. In still other embodiments, the SERM can be an estrogen receptor antagonist. In yet still other embodiments, the SERM can be an estrogen receptor partial antagonist. In some embodiments, the SERM can be a tissue-specific estrogen receptor agonist. In other embodiments, the SERM can be a tissue-specific estrogen receptor antagonist. Examples of suitable SERMs can be selected from lasofoxifene, tamoxifen, raloxifene, clomifene, enclomiphene, toremifene, ormeloxifene, bazedoxifene, ospemifene, fermarelle, afimoxifene, arzoxifene, and fulvestrant. In some embodiments, the SERM can be lasofoxifene. In some embodiments, the 5α-reductase inhibitor can be selected from finasteride, dutasteride, alfatradiol, bexlosteride, episteride, izonsteride, lapisteride, and turosteride.

In some embodiments, the SERM and the 5α-reductase inhibitor can be provided in a single dosage form. In other embodiments, the SERM and the 5α-reductase inhibitor can be provided in separate dosage forms. In some embodiments, the SERM and the 5α-reductase inhibitor can be provided at the same time. In other embodiments, the SERM and the 5α-reductase inhibitor can be provided at different times. In some embodiments, one or both of the SERM and the 5α-reductase inhibitor can be provided orally. In some embodiments, one or both of the SERM and the 5α-reductase inhibitor can be provided topically.

Some embodiments disclosed herein relate generally to a method of treating a disease, disorder or condition in men that can include administering an effective amount of a selective androgen receptor modulator compound and an effective amount of lasofoxifene, or a pharmaceutically acceptable salt, ester or prodrug of the foregoing.

Some embodiments disclosed herein relate generally to a method of treating a disease, disorder or condition that can include administering an effective amount of a selective androgen receptor modulator compound and an effective amount of an estrogen receptor modulator, or a pharmaceutically acceptable salt, ester or prodrug of the foregoing. Some embodiments disclosed herein relate generally to a method of modulating an androgen receptor and/or an estrogen receptor that can include contacting the androgen receptor and/or the estrogen receptor with an effective amount of a selective androgen receptor modulator compound and an effective amount of an estrogen receptor modulator, or a pharmaceutically acceptable salt, ester or prodrug of the foregoing, wherein the activity of the androgen receptor and/or the activity of the estrogen receptor is modulated.

In some embodiments, the SARM can be an androgen receptor agonist. In other embodiments, the SARM can be an androgen receptor partial agonist. In still other embodiments, the SARM can be an androgen receptor antagonist. In yet still other embodiments, the SARM can be an androgen receptor partial antagonist. In some embodiments, the SARM can be a tissue-specific androgen receptor agonist. In other embodiments, the SARM can be a tissue-specific androgen receptor antagonist. In some embodiments, the SARM can be selected from 6-(2(R)-(1(S)-hydroxy-2,2,2-trifluoroethyl)-5(R)-methyl-1-pyrrolidinyl)-4-trifluoromethyl-2(1H)-quinolinone, 4-(2(R)-(1(S)-hydroxy-2,2,2-trifluoroethyl)pyrrolidinyl)-2-trifluoromethyl-benzonitrile, and ostarine, or a pharmaceutically acceptable salt, ester or prodrug of the foregoing. In some embodiments, the SARM can have a structure of Formula I:

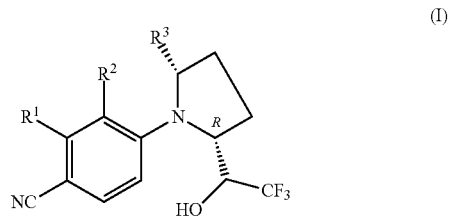

wherein: $R^1$ can be halogen, pseudohalogen, optionally substituted lower alkyl, optionally substituted haloalkyl or $NO_2$, $R^2$ can be hydrogen, halogen, pseudohalogen, optionally substituted lower alkyl or optionally substituted lower haloalkyl; and $R^3$ can be hydrogen, optionally substituted lower alkyl or optionally substituted lower haloalkyl, particularly hydrogen, or lower alkyl; or a pharmaceutically acceptable salt, ester or prodrug thereof. In some embodiments, $R^1$ can be lower haloalkyl or halogen. In some embodiments, $R^1$ can be $CF_3$, F, or Cl. In some embodiments, $R^2$ can be hydrogen or methyl. In some embodiments, $R^3$ can be hydrogen or methyl.

In some embodiments, the ER modulator can be an estrogen receptor agonist. In other embodiments, the ER modulator can be an estrogen receptor antagonist. In still other embodiments, the ER modulator can be an estrogen receptor partial agonist. In yet still other embodiments, the ER modulator can be an estrogen receptor partial antagonist. In some embodiments, the ER modulator can be a tissue-specific estrogen receptor agonist. In other embodiments, the ER modulator can be a tissue-specific estrogen receptor antagonist. In still other embodiments, the ER modulator can be an estrogen receptor sub-type selective modulator. In some embodiments, the ER modulator can be a SERM. In some embodiments, the ER modulator can be selected from among lasofoxifene, tamoxifen, raloxifene, clomifene, enclomiphene, toremifene, ormeloxifene, bazedoxifene, ospemifene, fermarelle, afimoxifene, arzoxifene, fulvestrant, estradiol, 17β-estradiol, estrone, estriol, ethynyl estradiol, mestranol, equine estrogens, synthetic estrogen analogs, and GTx-758. In some embodiments, the ER modulator can be lasofoxifene.

In some embodiments, the SARM and ER modulator can be provided in a single dosage form. In other embodiments, the SARM and ER modulator can be provided in a separate dosage forms. In some embodiments, the SARM and ER modulator can be provided at the same time. In other embodiments, the SARM and ER modulator can be provided at different times. In some embodiments, one or both of the SARM and the ER modulator can be provided orally. In some embodiments, one or both of the SARM and the ER modulator can be provided topically.

In some embodiments, a subject being treated can exhibit symptoms or signs of an AR/ER mediated condition. In some embodiments, a subject can be treated prophylactically to reduce or prevent the occurrence of a condition. In some embodiments, the disease, disorder or condition can be caused by an androgen deficiency or an estrogen deficiency; or the disease, disorder or condition can be caused hypoactivity, or subsensitivity of an androgen receptor or an estrogen receptor. In other embodiments, the disease, disorder or condition can be caused by hyperactivity of an androgen receptor or an estrogen receptor. In some embodiments, the disease, disorder or condition can be ameliorated by androgen replacement or estrogen replacement; or the disease, disorder or condition can be responsive to treatment with an androgen receptor modulator or estrogen receptor modulator; or the disease, disorder or condition can be responsive to stimulation of endogenous androgen production; or the disease, disorder or condition can be modulated through an androgen receptor and/or an estrogen receptor.

In some embodiments, a method and/or composition described herein can activate an androgen receptor and/or an estrogen receptor. In some embodiments, a method and/or composition described herein deactivate an androgen receptor and/or an estrogen receptor. In some embodiments, the androgen receptor and/or the estrogen receptor can be in a cell. In some embodiments, a method and/or composition described herein can exhibit AR agonist activity (such as AR agonist activity in some tissues). In some embodiments, a method and/or composition described herein can exhibit AR antagonist activity (such as AR agonist activity in some tissues).

The methods and compositions provided herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used in the treatment of a variety of conditions. For example, a method and compositions provided herein can be useful for treating and/or preventing a condition including, but not limited to, maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olfaction and taste); treatment of periodontal disease; treatment of wasting secondary to fractures and wasting in connection with COPD, chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondro-dysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD); reducing cachexia and protein loss due to chronic illness such as cancer or AIDS; treatment of hyperinsulinemia including nesidioblastosis; treatment of immunosuppressed subjects; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in subjects taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, BPH, adenomas and neoplasias of the prostate (e.g., advanced metastatic prostate cancer) and malignant tumor cells containing the AR, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and preterm labor; treatment of premenstrual syndrome; treatment of vaginal dryness; age related decreased T levels in men, male menopause, hypogonadism, male hormone replacement, male and female sexual dysfunction (e.g., erectile dysfunction, decreased sex drive, sexual well-being, decreased libido), hair loss, Reaven's Syndrome and the enhancement of bone and muscle performance/strength.

Further examples of conditions that can be treated and/or prevented by a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) include, but are not limited to, hypogonadism, wasting diseases, cancer cachexia, frailty, osteoporosis, hirsutism, acne, male-pattern baldness, prostatic hyperplasia, and cancer, including, but not limited to, various hormone-dependent cancers, including, without limitation, breast cancer.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used for male hormone replacement therapy. In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to stimulate hematopoiesis. In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used as an anabolic agent. In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to improve athletic performance.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be administered to a subject to treat a condition responsive to an AR modulator compound. The method can include administering to a subject having a condition responsive to an AR modulator compound. In some embodiments, the condition can be treated by agonizing the AR. In some embodiments, the condition can be treated by stimulating endogenous androgens to modulate the AR. In various embodiments, the condition treated can be selected from among hypogonadism, lower than normal T plasma levels, sexual arousal disorder, disorders of libido, muscle wasting, cachexia, sarcopenia, frailty, bone density loss, mood disorders (including lack of wellbeing, lack of vigor, anger, irritability, sadness, tiredness, nervousness and depression), impaired cognitive function (including verbal fluency and spatial memory), neurodegenerative disorders, including Alzheimer's disease, mild cognition impairment, Lewis body dementia, and frontal temporal dementia, xerophthalmia, metabolic disorders, including dyslipidemia, atherosclerosis, and non-insulin dependent diabetes (NIDDM), cardiovascular disorders including but not limited to hypertension, coronary artery disease, and myocardial perfusion, obesity, anemia, BPH, and schizophrenia. In other embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can be administered to a subject to prevent a condition in the subject. In some embodiments, the condition prevented can be bone density loss, xerophthalmia, metabolic disorders, including dyslipidemia, atherosclerosis, non-insulin dependent diabetes (NIDDM), cardiovascular disorders including hypertension, coronary artery disease, and myocardial perfusion, obesity, BPH, and/or prostate cancer.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to treat acne, male-pattern baldness, wasting diseases, hirsutism, hypogonadism, osteoporosis, impotence, obesity, and cancer. In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to stimulate hematopoiesis.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to treat and/or prevent a condition caused by androgen deficiency or a condition ameliorated by androgen replacement. In some embodiments, the condition can be selected from among abdominal obesity, Alzheimer's disease, anemia, an arthritic condition, atherosclerosis, BPH, cancer cachexia, cognitive decline, depression, metabolic syndrome, a muscular dystrophy, obesity, osteopenia, osteoporosis, a periodontal disease, prostate cancer, sexual dysfunction, sleep apnea, type II diabetes, bone fracture, frailty, wasting, aging skin, hypogonadism, post-menopausal symptoms in women, female sexual dysfunction, premature ovarian failure, atherosclerosis, hypercholesterolemia, hyperlipidemia, aplastic anemia and other hematopoietic disorders, pancreatic cancer, renal cancer, arthritis and joint repair.

1. Methods of Treating Muscle Wasting

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to treat, prevent, suppress, inhibit or reduce the incidence of muscle wasting in a subject. In some embodiments, the muscle wasting can be caused by a condition selected from among andropause, a spinal muscular atrophy, a muscular dystrophy, myasthenia gravis, AIDS cachexia, cardiac cachexia, cancer cachexia, cancer, COPD, emphysema, diabetes, HIV infection, AIDS, sepsis, tuberculosis, renal failure, heart failure, cardiomyopathy, bed rest, disuse, inactivity, microgravity, malnutrition, sarcopenia, aging, and space travel. In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can be used to treat muscular dystrophy, sarcopenia and/or frailty. In some embodiments, one or more additional agents can be used in a method and/or composition described herein, wherein the additional agent can be selected from among interleukin-10 (IL-10), interleukin-4 (IL-4), a TNF inhibitor, fluorinated 4-azasteroid derivatives, glial growth factors, acetylcholine receptor inducing activity (ARIA), heregulins, neu differentiation factor, and neuregulins (e.g., see U.S. Pat. Nos. 6,444,642 and 7,037,888).

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to treat and/or prevent a muscle-wasting condition associated with chronic illness.

Methods for identifying a subject in need of treatment for a muscular wasting disease are known in the art. For example, a subject in need of treatment for a muscular wasting disease will often generate less electrical activity during muscle contraction as compared to a healthy subject and this can be detected by electromyography. Alternative methods for diagnosis include, for example, blood tests and muscle biopsies. Suitably, blood tests can be run to determine the levels of various constituents of muscle and muscle fibers. For example, many muscular wasting diseases can be diagnosed by conducting a blood test to measure the level of creatinine in the blood. Creatinine is a breakdown product of creatine, which is an important constituent of muscle. Blood tests for determining the amount of creatine phosphokinase (CPK), which is an enzyme found predominantly in the heart, brain, and skeletal muscle, can be conducted to diagnose a subject in need for treatment of a muscular wasting disease. Specifically, when the total CPK level is substantially elevated, it usually indicates injury or stress to one or more of the heart, brain, and skeletal muscle. Subjects that may be affected by either Duchenne muscular dystrophy or Becker muscular dystrophy can be diagnosed by measuring the level of dystrophin. Typically, in subjects with either Duchenne muscular dystrophy or Becker muscular dystrophy, the level of dystrophin is deficient; but, in a subject with Duchenne muscular dystrophy, the level is more severely deficient.

Muscle biopsies also can be used to identify a subject in need of treatment for a muscular wasting disease. Generally, during a muscle biopsy, a small piece of muscle tissue is removed surgically for laboratory analysis. The analysis can reveal abnormalities in the muscle, such as inflammation, damage, or infection. The subject also can be diagnosed for a muscular wasting disease using magnetic resonance imagining (MRI). During an MRI, cross-sectional images of muscle are generated by a magnetic field and radio waves. Similar to the muscle biopsy analysis, the image generated by an MRI can reveal abnormalities in the muscle, such as inflammation, damage, or infection.

2. Methods of Improving Muscle Performance, Size and/or Strength

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be to increase muscle performance, muscle size, muscle strength, or any combination thereof in a subject. Further, in some embodiments, the increase in muscle performance, muscle size, muscle strength, or any combination thereof in a subject can occur without negative effects on other tissues of concerns and/or with a reduced side-effect profile.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can activate the function of the AR muscle tissue and block or inhibit the function of the AR in the prostate of a male individual or in the uterus of a female individual.

3. Methods of Improving Athletic Performance

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to improve athletic performance. In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used, for example, to shorten the time normally needed to recover from physical exertion or to increase muscle strength. Suitable athletes include, but are not limited to, horses, dogs and humans. In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be administered to an athlete engaged in a professional or recreational competition, including, but not limited to weight-lifting, body-building, track and field events, and any of various team sports.

4. Methods of Treating Bone-Related Conditions

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be to treat, prevent, suppress, inhibit or reduce the incidence of osteoporosis, osteopenia, gluco-corticoid-induced osteoporosis and/or bone fracture in a subject. In some embodiment, an effective amount of at least one other therapeutic agent can also be included in the method or composition. Examples of suitable other therapeutic agents include a bisphosphonate; an $\alpha_v\beta_3$ integrin receptor antagonist; a cathepsin inhibitor; a proton pump inhibitor; a PPARγ inhibitor; calcitonin; and osteoprotegerin. In some embodiment, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be for the treatment of osteoporosis. In some embodiment, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be for the treatment of osteopenia. In some embodiment, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be for the treatment of glucocorticoid-induced osteoporosis. In some embodiment, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used for the treatment of bone fracture.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can be used to activate the function of the AR in bone tissue and blocking or inhibit the function of the AR in the prostate of a male individual or in the uterus of a female individual.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be for increasing the strength of, or mass of a bone of a subject. In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be for promoting bone formation in a subject. In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be for preventing bone loss.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used for inhibiting and/or preventing a bone-related disorder in a subject. In some embodiment, the bone-related disorder can be osteoporosis. In other embodiments, the bone-related disorder can be osteopenia. In still other embodiments, the bone-related disorder can be increased bone resorption. In yet still other embodiments, the bone-related disorder can be a bone fracture. In some embodiment, the bone-related disorder can be bone frailty. In other embodiment, the bone-related disorder can be any combination of two of more of the following: osteoporosis, osteopenia, increased bone resorption, bone fracture and bone frailty.

In some embodiment, the osteoporosis can result from androgen deprivation. In other embodiments, the osteoporosis can follow androgen deprivation. In some embodiments, the osteoporosis can be primary osteoporosis. In other embodiments, the osteoporosis can be secondary osteoporosis. In still other embodiments, the osteoporosis can be postmenopausal osteoporosis. In yet still other embodiments, the osteoporosis can be juvenile osteoporosis. In some embodiments, the osteoporosis can be idiopathic osteoporosis. In other embodiments, the osteoporosis can be senile osteoporosis.

5. Methods of Treating and Preventing Cancer

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can be used for treating, preventing, suppressing, inhibiting or reducing the incidence of cancer in a subject. Certain exemplary cancers include, but are not limited to, breast cancer, uterine cancer, colorectal cancer, gastric carcinoma, glioma, head and neck squamous cell carcinoma, skin cancer, papillary renal carcinoma, leukemia, lymphoma, Li-Fraumeni syndrome, malignant pleural mesothelioma, melanoma, multiple myeloma, non-small cell lung cancer, synovial sarcoma, thyroid carcinoma, transitional cell carcinoma of urinary bladder, and prostate cancer, including, but not limited to prostatic hyperplasia.

In some embodiments, one or more other additional therapeutics is included in the combination. Suitable additional therapeutics include, but not limited to, anti-proliferative agents, such as paclitaxel, a paclitaxel derivative, taxanes and vinca alkaloids, anti-tumor agents, such as mitomycin C or doxorubicin, hormones and antagonists, such as adreno-corticosteroids (prednisone), progestins (hydroxyprogesterone caproate, medroprogesterone acetate and megestrol acetate), radionuclides, toxins and cytotoxic drugs, boron addends, chemotherapy agents, photodynamic therapy dyes, and antibiotics or combinations thereof to treat cancer. Many toxins and cytotoxic drugs are known in the art that have cytotoxic effects on cells, any of which can be used in connection with the methods provided herein. Examples of known cytotoxic agents useful in the present methods are listed, for example, in Goodman et al., "The Pharmacological Basis of Therapeutics," Sixth Edition, A. G. Gilman et al., eds., Macmillan Publishing Co., New York (1980). These include, but are not limited to, adrenocortical suppressants, such as mitotane; alkyl sulfonates, such as busulfan; ethylenimine derivatives, such as thiotepa; nitrosoureas, such as carmustine, lomustine, semustine and streptozocin; folic acid analogs, such as methotrexate; methyl hydrazine derivatives, such as procarbazine; nitrogen mustards, such as mechlorethamine, cyclophosphamide, melphalan, uracil mustard and chlorambucil; purine analogs, such as mercaptopurine and thioguanine; pyrimidine analogs, such as fluorouracil, cytarabine and azaribine; substituted urea compounds, such as hydroxyurea; taxol; triazenes, such as dacarbazine; and vinca alkaloids, such as vinblastine and vincristine.

Any antibiotic known in the art, such as aminoglycosides, bleomycin, cephalosporins and other beta-lactam antibiotics, chloramphenicol, clindamycin, dactinomycin, daunorubicin, doxorubicin, fusidic acid, macrolides, metronidazole, mithramycin, mitomycin, mupirocin, penicillins, rifamycins, sulfonamides, tetracyclines, trimethoprim and beta-lactam inhibitors, can be included in the formulation. Drugs that interfere with intracellular protein synthesis also can be used in the methods provided herein; such drugs are known to those skilled in the art and include puromycin, cycloheximide, and ribonuclease.

6. Methods of Providing Hormone Therapy

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used for providing hormone therapy to a subject. In some embodiments, a method and/or composition described herein can effect a change in an androgen-dependent condition by modulating the activity of the AR.

7. Methods of Treating Postmenopausal Conditions

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can be used for treating, preventing, suppressing, inhibiting or reducing the incidence of postmenopausal conditions in a subject. Examples of suitable postmenopausal conditions include, but is not limited to, loss of libido, decreased sexual activity, diminished feelings of physical well-being, fatigue and hot flashes. In some embodiments, one or more estrogens can also be included in a method and/or composition described herein. Examples of estrogens include estrone, 2-hydroxyestrone, 2-methoxyestrone, 4-hydroxyestrone, 15-α-hydroxyestrone, 16-α-hydroxyestrone, 16-β-hydroxyestrone, estradiol (17β-estradiol), 2-hydroxy-estradiol, 2-methoxy-estradiol, 4-hydroxy-estradiol, 16-oxoestradiol, estriol, 16-epiestriol and 17-epiestriol or combinations thereof. In some embodiments, one or more estrogenic compounds can be included in a method and/or composition described herein. A non-limiting list of estrogenic compounds includes estradiol valerate, estrone, estrone sulfate, an estrone sulfate piperazine salt or an ester thereof, or a synthetic estrogen. In some embodiments, one or more agents selected from among alendronate, calcitonin, clodronate, clomiphene, clomiphene citrate, clonidine, conjugated estrogen, natural estrogen, synthetic estrogen, ethinyl estradiol, estradiol, enclomiphene, enclomiphene citrate, etidronate, ibandronate, medroxyprogesterone acetate, megestrol acetate, norethindrone acetate, pamidronate, progesterone, residronate, tiludronate, zuclomiphene, zuclomiphene citrate and combinations thereof, can be include in a method and/or composition described herein.

8. Methods of Treating Hematopoietic Disorders

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used for treating, preventing, suppressing, inhibiting or reducing the incidence of a hematopoietic disorder in a subject. Examples of hematopoietic disorders include, but not limited to, anemia, leukemia, and hematopoietic conditions caused by bone marrow transplantation or chemo-/radiation therapy. In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be increase the number of red blood cells in a subject in need thereof. In some embodiments, the hematopoietic disorder can be selected from anemia, thrombocytopenia or neutropenia in a subject. In some embodiments, at least one hematopoietic cytokine can be also included in a method and/or composition described herein. In some embodiments, the hematopoietic cytokine can be selected from among erythropoietin, granulocyte-colony stimulating factor, granulocyte-macrophage-colony stimulating factor, interleukin-1, interleukin-3, interleukin-4, interleukin-5, interleukin-7, interleukin-9, interleukin-11, macrophage-colony stimulating factor, stem cell factor and thrombopoietin.

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be for increasing serum EPO levels in a subject.

9. Methods of Treating Neurodegenerative Diseases and Disorders

In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be for treating, preventing, suppressing, inhibiting or reducing the incidence of a neurodegenerative disease or disorder in a subject. In some embodiments, the neurodegenerative disorder can be Alzheimer's disease. In some embodiments, a method and/or composition described herein can prevent the onset or delaying the progression of Alzheimer's disease in subjects.

In some embodiments, a therapeutically-effective amount of a compound that inhibits the formation or release, or eliminates amounts of β-amyloid and/or tau protein can be included in a method and/or composition described herein. Any of the known inhibitors of the formation or release of β-amyloid can be used in the methods, including, but not limited to, compounds described in U.S. Pat. App. Pub. Nos. U.S. 2002/0025955, 2002/0022621 and U.S. 2003/0114496 and in WO 03/018543, WO 01/53255, WO 01/66564, WO 01/70677, WO 01/90084, WO 01/77144, WO 02/30912, WO 02/36555, WO 02/081435, WO 02/081433, WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391 and WO 02/057252.

10. Methods of Treating Cognitive Impairment

Some embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) that can be used for treating, preventing, suppressing, inhibiting or reducing the incidence of cognitive impairment in a subject.

11. Methods of Treating Depression

Other embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) that can be used for treating, preventing, suppressing, inhibiting or reducing the incidence of depression in a subject. The methods include administering to a subject having cognitive impairment one composition or pharmaceutically acceptable salts or prodrugs thereof, in an amount effective to treat depression.

12. Methods of Treating Obesity

Some embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) that can be used for treating, preventing, suppressing, inhibiting or reducing the incidence of obesity in a subject. In some embodiments, the method and/or composition includes AR agonist, which can treat a male subject with abdominal adiposity. In some embodiments, a method and/or composition described herein can be to stimulate endogenous T production and thereby treat a subject with abdominal obesity.

13. Methods of Treating Insulin Resistance and Diabetes

Some embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) that can be used for treating, preventing, suppressing, inhibiting or reducing the incidence of insulin resistance in a subject. Other embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) that can be used for treating, preventing, suppressing, inhibiting or reducing the incidence of type 2 diabetes in a subject. In some embodiments, an effective amount of an anti-diabetic drug can be used in combination with a method and/or composition described herein to treat diabetes. Examples of anti-diabetic drugs include, but not limited to, thiazolidinedione-type drugs such as pioglitazone or rosiglitazone, sulfonylurea-type drugs, such as chlorpropamide, glimepiride, glipizide, glyburide or tolbutamide, a biguanide-type drug such as metformin, a GLP-1 analog drug such as exenatide, a DPP4 inhibitor drug such as sitagliptin and linagliptin, an insulin product such as insulin glargine, a SGLT2 inhibitor drug such as canagliflozin, acarbose, repaglinide, nateglinide, tolazamide or combinations thereof.

Some embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) that can be used for treating, preventing, suppressing, inhibiting or reducing the incidence of arterial hypertension, hyper-insulineamia, hyperglycaemia, type 2 diabetes or dyslipidaemia characteristically appearing with insulin resistance.

14. Methods of Treating Sexual Dysfunction

Some embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) that can be used for treating, preventing, suppressing, inhibiting or reducing the incidence of sexual dysfunction in a subject. In some embodiments, the sexual dysfunction can be male erectile dysfunction. In other embodiments, the sexual dysfunction can be impotence.

Other embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) that can be used for increasing the libido of a subject.

15. Methods of Treating Arthritic Conditions and Inflammatory Disorders

Some embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) that can be used for treating, preventing, suppressing, inhibiting or reducing the incidence of an arthritic condition or inflammatory disorder. In some embodiments, the arthritic condition or inflammatory disorder can be selected from among osteoarthritis, Behcet's disease, bursitis, tendonitis, CPPD deposition disease, carpal tunnel syndrome, Ehlers-Danlos syndrome, fibromyalgia, gout, infectious arthritis, inflammatory bowel disease, juvenile arthritis, lupus erythematosus, Lyme disease, Marfan syndrome, myositis, osteoarthritis, osteogenesis imperfecta, osteonecrosis, polyarteritis, polymyalgia rheumatica, psoriatic arthritis, Raynaud's phenomenon, reflex sympathetic dystrophy syndrome, Reiter's syndrome, rheumatoid arthritis, scleroderma and Sjogren's syndrome. In some embodiment, a method and/or composition described herein can be used for treating, preventing, suppressing, inhibiting or reducing the incidence of osteoarthritis. In some embodiments, one or more drugs or agents known to treat or prevent arthritic conditions can be also included in a method and/or composition described herein. Examples of drugs or agents known to treat or prevent arthritic conditions include corticosteroids, cytotoxic drugs (or other disease modifying or remission inducing drugs), gold treatment, methotrexate, aspirin, NSAIDs, COX-2 inhibitors and DMARDs (Disease-Modifying Anti-Rheumatic Drugs).

16. Methods of Improving Lipid Profile

Some embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) that can be used for improving the lipid profile in a subject. In some embodiments, an anti-cholesterol agent or lipid-lowering agent can be included in a method and/or composition described herein. A non-limiting list of an anti-cholesterol agents and lipid-lowering agents include β-hydroxy-β-methylbutyric acid, lactoferrin, cholestryramine, cholestipol, colesevalam, nicotinic acid, fibric acids (gemfibrozil, fenofibrate and clofibrate) and HMG-coA reductase inhibitors (lovastatin, pravastatin, simvastatin, fluvastatin, atorvastatin and cerivastatin).

17. Methods of Treating Atherosclerosis

Some embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) that can be used for treating, preventing, suppressing, inhibiting or reducing the incidence of atherosclerosis and its associated diseases (for example, cardiovascular disorders, cerebrovascular disorders, peripheral vascular disorders, and intestinal vascular disorders) in a subject.

18. Methods of Treating Conditions Related to Androgen Decline

Other embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) that can be used for treating, preventing, suppressing, inhibiting or reducing the incidence of a condition related to androgen decline. In some embodiments, the condition can be selected from among fatigue, depression, decreased libido, sexual dysfunction, erectile dysfunction, hypogonadism, osteoporosis, hair loss, obesity, sarcopenia, osteopenia, anemia, alterations in mood and cognition. In some embodiments, the condition related to androgen decline is in a male subject.

19. Methods of Treating Conditions Related to Androgen Deficiency

Other embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) that can be used for treating, preventing, suppressing, inhibiting or reducing the incidence of a condition related to androgen deficiency. In some embodiment, the condition can be selected from among sexual dysfunction, decreased sexual libido, sarcopenia, osteopenia, osteoporosis, alterations in cognition and mood, depression, anemia, hair loss, obesity, endometriosis, breast cancer, uterine cancer and ovarian cancer. In some embodiments, the condition related to androgen decline is in a female subject.

20. Other

Some embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used for treating arterial hypertension, hyper-insulinaemia, hyperglycemia or dyslipidemia in a subject.

Other embodiments disclosed herein relate generally to a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be used to treat a condition selected from among angina, coronary artery disease, arteriosclerosis, atherosclerosis, obesity, diabetes, syndrome X, glucose intolerance, insulin resistance, hypercholesterolemia, hyperlipoproteinemia, hyperglycemia, hyperinsulinemia, hyperlipidemia, glaucoma, hypertension, hypertriglyceridemia, renal disease, thrombosis, peripheral vascular disease, vascular wall damage, stroke, dyslipidemia, diabetic dyslipidemia, mixed dyslipidemia and nonalcoholic fatty liver disease.

Compositions and method described herein include a combination of two therapeutic classes of compounds that can achieve a superior benefit/risk ratio. In some embodiments, the compositions and methods described herein can be used to activate the function of the AR and/or ER in a subject. For example, compositions and methods described herein can activate the function of the AR and/or ER in bone, muscle, and/or CNS tissues, reduce or inhibit (antagonize) the function of the AR in sebaceous glands, reduce or inhibit the function of the AR in the prostate of a male individual and reduce or inhibit the function of the ER in the uterus/breast of a female individual, and/or to have neutral or beneficial effects on the cardiovascular system.

Some embodiments described herein relate generally to a composition that can include a selective estrogen receptor modulator compound and an effective amount of a 5α-reductase inhibitor. In some embodiments, the SERM compound can have CNS activity to stimulate endogenous testosterone production in men and the 5α-reductase inhibitor can be a steroidal 5α-reductase inhibitor. In some embodiments, the SERM compound can increase biologically active T level in circulation (free-T concentration). In some embodiments, the composition can display therapeutic benefits in muscle, bone, and CNS but generally do not display adverse effects in prostate, sebaceous glands, and cardiovascular system.

Suitable SERM compounds are tissue-selective ER mixed agonists/antagonists that have centrally ER antagonistic activity to stimulate endogenous T production in men without over stimulation of SHBG production in the liver and with or without measurable elevation of LH/FSH. Representative SERM compounds are lasofoxifene, tamoxifen, raloxifene, clomifene, enclomiphene, toremifene, ormeloxifene, bazedoxifene, ospemifene, fermarelle, afimoxifene, arzoxifene, fulvestrant, and analogs of the aforementioned.

Suitable 5α-reductase inhibiting compounds are described herein and include finasteride, dutasteride, alfatradiol, bexlosteride, episteride, izonsteride, lapisteride, turosteride and analogs of the aforementioned.

Some embodiments described herein relate generally to a composition that includes a selective androgen receptor modulator (SARM) compound and an effective amount of an estrogen receptor (ER) modulator. In some embodiments, the combination of a SARM and ER modulator can have CNS activity to stimulate endogenous sex hormone production. In some embodiments, the combination of a SARM and ER modulator can display therapeutic benefits in muscle, bone, and CNS but generally do not display adverse effects in prostate, sebaceous glands, and cardiovascular system for uses in men. In women, the combination of a SARM and ER modulator can display therapeutic benefits in muscle, bone, breast, uterus, vagina, and CNS but generally do not display adverse effects in sebaceous glands and cardiovascular system.

Among the SARM compounds provided herein are a class of compounds that display tissue selective anabolic activities in muscle, bone, and CNS with reduced androgenic activities in prostate and sebaceous glands. Compounds provided herein display AR agonist activity with $EC_{50}$ and/or antagonist activity with $IC_{50}$ values generally less than 1 micromolar in one of the known in vitro assays. Representative compounds of the therapeutic class are 6-(2(R)-(1(S)-hydroxy-2,2,2-trifluoroethyl)-5(R)-methyl-1-pyrrolidinyl)-4-trifluoromethyl-2(1H)-quinolinone, 4-(2(R)-(1(S)-hydroxy-2,2,2-trifluoroethyl)pyrrolidinyl)-2-trifluoromethyl-benzonitrile, ostarine, analogs of the aforementioned, and compounds having a structure of Formula I:

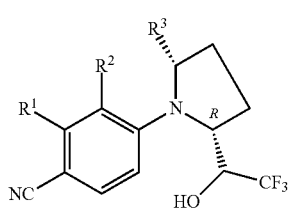

(I)

where $R^1$ can be halogen, pseudohalogen, optionally substituted lower alkyl, optionally substituted haloalkyl or $NO_2$, particularly lower haloalkyl or halogen, and in particular is $CF_3$, F, or Cl; $R^2$ can be hydrogen, halogen, pseudohalogen, optionally substituted lower alkyl or optionally substituted lower haloalkyl, particularly hydrogen or methyl; and $R^3$ can be hydrogen, optionally substituted lower alkyl or optionally substituted lower haloalkyl, particularly hydrogen, or lower alkyl, and in particular hydrogen or methyl.

Among the ER modulating compounds provided herein are classes of compounds that display tissue selective ER agonist/antagonist activity (SERMs) or traditional ER agonist profile similar to that of estradiol (estrogens) or ER sub-type selective modulating activity, and display ER antagonist activity with $IC_{50}$ and/or agonist activity with $EC_{50}$ values generally less than 1 micromolar for at least one ER subtype in one of the known in vitro assays. In some embodiments, the ER modulating compound can be a SERM compound. The SERM compound can simulate endogenous sex hormone production via a gonadal negative-feedback mechanism. The ER modulating compound can stimulate endogenous sex hormone production via a gonadal positive-feedback mechanism, and the ER sub-type selective compounds can stimulate endogenous sex hormone production via a subtype receptor mediated mechanism. Representative ER modulators compounds are lasofoxifene, tamoxifen, raloxifene, clomifene, enclomiphene, toremifene, ormeloxifene, bazedoxifene, ospemifene, fermarelle, afimoxifene, arzoxifene, fulvestrant, estradiol, 17β-estradiol, estrone, estriol, ethynyl estradiol, mestranol, equine estrogens, synthetic estrogen analogs, GTx-758, analogs of the aforementioned, and combinations of the aforementioned.

In some embodiments, the combination of a SARM compound with an ER modulator can have the benefit of exhibiting anabolic activity in bone and muscle, beneficial activity in CNS, neutral or antagonist activity in prostate and sebaceous glands, and/or neutral or beneficial effects in cardiovascular system. For use in females, the combination of a SARM compound with an ER modulator can offer the additional benefits in bone, breast, vagina, and/or uterus via an ER mediated mechanism.

For examples, compound (5R,6S)-6-phenyl-5-[4-(2-pyrrolidin-1-ylethoxy)phenyl]-5,6,7,8-tetrahydronaphthalen-2-ol (lasofoxifene) is a potent SERM with $IC_{50}$ of 11 nM binding affinity to ER and has demonstrated beneficial effects in postmenopausal women with reduced risks of nonvertebral and vertebral fractures, ER-positive breast cancer, coronary heart disease, and stroke (e.g. see S. R. Cummings, et al. NEJM 362(8): 686-96 (2011)); Compound N-(1,1-dimethylethyl)-3-oxo-(5α,17β)-4-azaandrost-1-ene-17-carboxamide (finasteride) is a potent 5α-reductase inhibitor with $IC_{50}$ of 42 nM and 3 nM for 5α-reductase types I and II isoenzymes and in clinic reduces prostate DHT level up to 85-90% (e.g., see G. Bartsch, et al. European Urology 37(4): 367-80 (2000)); and 4-(2(R)-(1(S)-hydroxyl-2,2,2-trifluoroethyl)pyrrolidinyl)-2-trifluoromethyl-benzonitrile is a potent SARM and has demonstrated favorable safety and pharmacokinetic profiles in healthy young men (see S. Basaria, et al. J Gerontol A Biol Sci Med Sci 68(1): 87-95 (2013)).

In some embodiments, a method and/or composition provided herein can include an effective amount of lasofoxifene in combination with an effective amount of 5α-reductase inhibitor such as finasteride or dutasteride. For example, an effective amounts of lasofoxifene and finasteride or an effective amount of lasofoxifene and dutasteride.

In some embodiments a method and/or composition provided herein can include an effective amount of lasofoxifene in combination with an effective amount of a SARM compound such as 6-(2(R)-(1(S)-hydroxy-2,2,2-trifluoroethyl)-5(R)-methyl-1-pyrrolidinyl)-4-trifluoromethyl-2(1H)-quinolinone, 4-(2(R)-(1(S)-hydroxy-2,2,2-trifluoroethyl)pyrrolidinyl)-2-trifluoromethyl-benzonitrile, or ostarine.

In some embodiments a method and/or composition provided herein can include an effective amount of 4-(2(R)-(1 (S)-hydroxyl-2,2,2-trifluoroethyl)-pyrrolidinyl)-2-trifluoromethylbenzonitrile (Formula I, $R^1=CF_3$, $R^2=R^3=H$) in combination with an effective amount of an ER modulating compound, such as lasofoxifene or enclomiphene.

In some embodiments, a method and/or composition provided herein can include an effective amount of 6-(2(R)-(1(S)-hydroxy-2,2,2-trifluoroethyl)-5(R)-methyl-1-pyrrolidinyl)-4-trifluoromethyl-2(1H)-quinolinone in combination with an effective amount of an ER modulating compound, such as lasofoxifene or enclomiphene.

The amount each of compound utilized in a method and/or composition described herein can be varied depending on the relative activity of the compounds and specific therapeutic indications. As described herein, other therapeutic agents can be used in combination with a method and/or combination described herein. The amount of each compound used in a method and/or composition described herein can be an amount sufficient to exert a therapeutically useful effect in the absence of undesirable side effects on the subject treated.

In some embodiments, a combination of compounds described herein (e.g., a combination of an effective amount of a selective estrogen receptor modulator and an effective amount of a 5α-reductase inhibitor, or a pharmaceutically acceptable salt, ester or prodrug of the foregoing, or an effective amount of a selective androgen receptor modulator compound and an effective amount of an estrogen receptor modulator, or a pharmaceutically acceptable salt, ester or prodrug of the foregoing) can behave as an AR agonist in some tissue(s). In other embodiments, a combination of compounds described herein (e.g., a combination of an effective amount of a selective estrogen receptor modulator and an effective amount of a 5α-reductase inhibitor, or a pharmaceutically acceptable salt, ester or prodrug of the foregoing, or an effective amount of a selective androgen receptor modulator compound and an effective amount of an estrogen receptor modulator, or a pharmaceutically acceptable salt, ester or prodrug of the foregoing) can behave an AR antagonist in some tissue(s). In still other embodiments, a combination of compounds described herein (e.g., a combination of an effective amount of a selective estrogen receptor modulator and an effective amount of a 5α-reductase inhibitor, or a pharmaceutically acceptable salt, ester or prodrug of the foregoing, or an effective amount of a selective androgen receptor modulator compound and an effective amount of an estrogen receptor modulator, or a pharmaceutically acceptable salt, ester or prodrug of the foregoing) can behave behaves as AR neutral in some tissue(s).

Other embodiments disclosed herein relate generally to a method for replacing testosterone in a male subject that can include administering to the male subject an effective amount of laxofoxifene, or a pharmaceutically acceptable salt, ester or prodrug thereof, wherein the administration of laxofoxifene, or a pharmaceutically acceptable salt, ester or prodrug thereof, of increases the amount of testosterone in the male subject.

The amount of laxofoxifene, or a pharmaceutically acceptable salt thereof, can vary. In some embodiments, the effective amount of laxofoxifene, or a pharmaceutically acceptable salt thereof, can be in the range of about 0.005 mg to about 100 mg. In other embodiments, the effective amount of laxofoxifene or a pharmaceutically acceptable salt thereof, can be in the range of about 0.01 mg to about 10 mg. In still other embodiments, the effective amount of laxofoxifene or a pharmaceutically acceptable salt thereof, can be in the range of about 0.05 mg to about 5 mg. In yet still other embodiments, the effective amount of laxofoxifene or a pharmaceutically acceptable salt thereof, can be at least 0.1 mg.

Laxofoxifene, or a pharmaceutically acceptable salt thereof, can be administered by methods known to those skilled in the art. In some embodiments, the effective amount of laxofoxifene, or a pharmaceutically acceptable salt thereof, can be administered in a single dose daily, or a single dose weekly, or a single dose monthly, or a single dose trimonthly. In some embodiments, the laxofoxifene, or a pharmaceutically acceptable salt thereof, can be administered orally, or parenterally.

SERMS have been shown to stimulate endogenous testosterone (T) production in men via perturbation of the gonadal axis. In some embodiments, the increase of the amount of testosterone can be maintained at least 7 days after being administered the single dose of laxofoxifene. In some embodiments, the increase of the amount of testosterone can be maintained at least 14 days after being administered the single dose of laxofoxifene. In some embodiments, the increase of the amount of testosterone can be maintained at least 28 days after being administered the single dose of laxofoxifene.

The compositions are formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds of the compositions described above are formulated into pharmaceutical compositions using techniques and procedures well known in the art (see, e.g., Ansel *Introduction to Pharmaceutical Dosage Forms*, 4$^{th}$ Edition (1985), 126).

In some embodiments, a composition provided herein is prepared using known techniques, including, but not limited to mixing, dissolving, granulating, dragée-making, levigating, emulsifying, encapsulating, entrapping or tabletting processes.

In the compositions, effective concentrations of one or more compounds or pharmaceutically acceptable derivatives is (are) mixed with a suitable pharmaceutical carrier or vehicle. The compounds of the compositions can be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with androgen and/or estrogen receptor activities or in which the receptor activities are implicated.

Typically, the compositions are formulated for single dosage administration. To formulate a composition, the weight fraction of compounds are dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds can be formulated as the sole pharmaceutically active ingredient(s) in the composition or can be combined with other active ingredients. Liposomal suspensions, including tissue-targeted liposomes, such as tumor-targeted liposomes, also can be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) can be formed by drying down egg phosphatidyl choline and brain phosphatidyl serine (7:3 molar ratio) on the inside of a flask. A solution of a composition provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The concentration of the compound(s) provided herein in the composition will depend on absorption, inactivation and excretion rates of the compounds, the physicochemical characteristics of the compounds, the dosage schedule, and amount administered as well as other factors known to those of skill in the art. For example, the amount that is delivered is sufficient to ameliorate one or more of the symptoms of diseases or disorders associated with androgen/estrogen receptor activities or in which the receptor activities are implicated, as described herein.

The effective amounts of the compositions provided herein can be determined by one of ordinary skill in the art, and includes exemplary dosage amounts for a mammal of from about 0.001 to 10 mg/kg of body weight of each active ingredient per day, which can be administered in a single dose or in the form of individual divided doses, such as from 1 to 4 times per day. It will be understood that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. In some embodiments, the daily dosage of the compound(s) provided herein can be varied over a wide range from about or 0.01 to about or 1000 mg per adult human per day per active ingredient. For example, dosages can range from about or 0.01 to about or 200 mg/day per active ingredient. In some embodiments, the dosage can range from 0.02 mg to 20 mg per day per active ingredient. In some embodiments, the dosage can range from 0.05 mg to 10 mg per day per active ingredient. In some embodiments, the daily dosage can be 0.01 mg, 0.05 mg, 0.1 mg, 0.25 mg, 0.5 mg, 0.75 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8 mg, 8.25 mg, 8.5 mg, 8.75 mg, 9 mg, 9.25 mg, 9.5 mg, 9.75 mg, and 10 mg per active ingredient. For oral administration, the pharmaceutical compositions can be provided in the form of unit dosages such as tablets or capsules or liquids including from about or 0.01 to about or 1000 mg per active ingredient, such as for example, 0.01, 0.05, 0.075, 0.1, 0.25, 0.5, 0.75, 1, 2, 2.5, 3, 4, 5, 6, 7, 8, 9, 10, 15, 20, 25, 50, 75, 100, 125, 150, 175, 180, 190, 200, 225, 250, 300, 400, 500, 750, 800, 850, 900, 950 and 1000 milligrams each of the active ingredients for the symptomatic adjustment of the dosage to the subject to be treated. In some embodiments, the compositions can be provided in the form of unit dosages such as tablets or capsules or liquids including from about or 0.01 to about or 1000 µg per active ingredient, such as for example, 0.01, 0.05, 0.075, 0.1, 0.25, 0.5, 0.75, 1, 2.5, 3, 4, 5, 6, 7, 8, 9, 10, 15, 20, 25, 50, 75, 100, 125, 150, 175, 180, 190, 200, 225, 250, 300, 350, 400, 450, 500, 550, 600, 650, 700, 750, 800, 850, 900, 950 and 1000 micrograms per active ingredient for the symptomatic adjustment of the dosage to the subject to be treated.

The composition can be administered at once, or can be divided into a number of smaller doses to be administered at intervals of time. The individual components of a combination described herein can be administered separately at different times during the course of therapy or concurrently in divided or single combination forms. The methods disclosed herein therefore are to be understood as embracing all such regimes of simultaneous or alternating treatment.

It is understood that the precise dosage and duration of treatment is a function of the disease being treated and can be determined empirically using known testing protocols or by extrapolation from in vivo or in vitro test data. It is to be noted that concentrations and dosage values also can vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the compounds, compositions, methods and other subject matter provided herein.

Pharmaceutically acceptable derivatives include acids, bases, enol ethers and esters, salts, esters, hydrates, solvates and prodrug forms. The derivative is selected such that its pharmacokinetic properties are superior to the corresponding neutral compounds.

Thus, effective concentrations or amounts of the compounds described herein or pharmaceutically acceptable derivatives or prodrugs thereof are mixed with a suitable pharmaceutical carrier or vehicle for systemic, topical or local administration to form pharmaceutical compositions. The compounds provided herein are included in an amount effective for ameliorating one or more symptoms of, or for treating or preventing diseases or disorders associated with androgen and/or estrogen receptor activities or in which the receptor activities are implicated, as described herein. The concentration of the compounds in a composition described herein will depend on absorption, inactivation, excretion rates of the active compounds, the dosage schedule, amount administered, particular formulation as well as other factors known to those of skill in the art.

The compositions are intended to be administered by a suitable route, including orally in the form of capsules, tablets, granules, powders or liquid formulations including syrups; parenterally, such as subcutaneously, intravenously, intramuscularly, with intersternal injection or infusion techniques (as sterile injectable aqueous (aq.) or non-aqueous solutions or suspensions); nasally, such as by inhalation spray; topically, such as in the form of a cream or ointment; rectally, such as in the form of suppositories; liposomally; intestinally and locally. The compositions can be in liquid, semi-liquid or solid form and are formulated in a manner suitable for each route of administration. In certain embodiments, administration of the formulation includes parenteral and oral modes of administration. In some embodiments, the compositions can be administered orally.

In some embodiments, the compositions provided herein are solid (e.g., a powder, tablet, and/or capsule). In some of such embodiments, a solid pharmaceutical composition including one or more compounds provided herein is prepared using ingredients known in the art, including, but not limited to, starches, sugars, diluents, granulating agents, gums, lubricants, binders, and disintegrating agents.

In some embodiments, a composition provided herein can be formulated as a depot preparation. Certain of such depot preparations are typically longer acting than non-depot preparations. In certain embodiments, such preparations are administered by implantation (for example, subcutaneously or intramuscularly) or by intramuscular injection. In some embodiments, depot preparations can be prepared using suitable polymeric or hydrophobic materials (for example, an emulsion in an acceptable oil) or ion exchange resins, or as sparingly soluble derivatives, for example, as a sparingly soluble salt.

In some embodiments, a composition provided herein can include a delivery system. Examples of delivery systems include, but are not limited to, liposomes and emulsions. Certain delivery systems are useful for preparing certain compositions including those including hydrophobic compounds. In some embodiments, certain organic solvents, such as dimethylsulfoxide, are used.

In some embodiments, a composition provided herein includes a co-solvent system. Certain of such co-solvent systems include, for example, benzyl alcohol, a nonpolar surfactant, a water-miscible organic polymer, and an aqueous phase. In some embodiments, such co-solvent systems are used for hydrophobic compounds. A non-limiting example of such a co-solvent system is the VPD co-solvent system, which is a solution of absolute ethanol including 3% w/v benzyl alcohol, 8% w/v of the nonpolar surfactant Polysorbate 80™, and 65% w/v polyethylene glycol 300. The proportions of such co-solvent systems can be varied considerably without significantly altering their solubility and toxicity characteristics. Furthermore, the identity of co-solvent components can be varied: for example, other surfactants can be used instead of Polysorbate 80™; the fraction size of polyethylene glycol can be varied; other biocompatible polymers can replace polyethylene glycol, e.g., polyvinyl pyrrolidone; and other sugars or polysaccharides can substitute for dextrose.

In some embodiments, solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfate; chelating agents, such as ethylenediamine-tetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds can be used. Such methods are known to those of skill in this art, and include, but are not limited to, using cosolvents, such as dimethylsulfoxide (DMSO), using surfactants, such as surfactants that include polyoxyethylene derivatives of sorbitan monolaurate, such as TWEEN® or polysorbate surfactants, or dissolution in aqueous sodium bicarbonate. Derivatives of the compounds, such as prodrugs of the compounds also can be used in formulating effective compositions.

In some embodiments, a composition provided herein can include a sustained release system. A non-limiting example of such a sustained-release system is a semipermeable matrix of solid hydrophobic polymers. In some embodiments, sustained release systems can, depending on their chemical nature, release compounds over a period of hours, days, weeks or months.

In some embodiments, upon mixing or addition of the compound(s), the resulting mixture can be a solution, suspension or emulsion. The form of the resulting mixture depends upon a number of factors, including the intended mode of administration and the solubility of the compound in the selected carrier or vehicle. The effective concentration is sufficient for ameliorating the symptoms of the disease, disorder or condition treated and can be empirically determined.

The compositions are provided for administration to humans and animals in unit dosage forms, such as tablets, capsules, pills, powders, granules, sterile parenteral solutions or suspensions, and oral solutions or suspensions, and oil-water emulsions including suitable quantities of the compounds or pharmaceutically acceptable derivatives thereof. The pharmaceutically active compounds and derivatives thereof are typically formulated and administered in unit dosage forms.

The composition can include, in addition to the two compound provided herein, other ingredients, such as, but not limited to, a diluent such as lactose, sucrose, dicalcium phosphate, or carboxymethylcellulose; a lubricant, such as magnesium stearate, calcium stearate and talc; and a binder such as starch, natural gums, such as gum acacia, gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols and ethanol, to thereby form a solution or suspension. If desired, the pharmaceutical composition to be administered also can include minor amounts of nontoxic auxiliary substances such as wetting agents, emulsifying agents, or solubilizing agents, or pH buffering agents, for example, acetate or sodium citrate, or cyclodextrin derivatives, sorbitan monolaurate, triethanolamine sodium acetate, triethanolamine oleate. Actual methods of preparing such dosage forms are known, or will be apparent, to those skilled in this art; for example, see *Remington's Pharmaceutical Sciences*, Mack Publishing Company, Easton, Pa., 15$^{th}$ edition (1975). The pharmaceutical composition or formulation to be administered will, in any event, include a quantity of the active compounds in an amount sufficient to alleviate the symptoms of the treated subject.

Dosage forms or compositions can be prepared to include one or more compounds provided herein in the range of 0.005% to 100% with the balance made up from non-toxic carrier. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium croscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions can include 0.001%-100% active ingredient, in one embodiment 0.1-85%, in another embodiment 75-95%. In some embodiments, the pharmaceutical compositions include 1-10% active ingredients. In some embodiments, the pharmaceutical compositions include 10-25% active ingredients. In some embodiments, the composition can include 15-35% active ingredients. In some embodiments, the composition can include 40-60% active ingredients. In some embodiments, the composition can include 50-75% active ingredients. In some embodiments, the active ingredients can be present at 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

In some embodiments, the compounds can be administered in a form suitable for immediate release or extended release. Immediate release or extended release can be achieved with suitable pharmaceutical compositions or, particularly in the case of extended release, with devices such as subcutaneous implants or osmotic pumps. Exemplary compositions for topical administration include a topical carrier such as a mineral oil gelled with polyethylene (e.g., PLASTIBASE®).

In some embodiments, compounds provided herein can be provided as pharmaceutically acceptable salts with pharmaceutically compatible counter-ions. Pharmaceutically compatible salts can be formed with many acids, including, but not limited to, hydrochloric, sulfuric, acetic, citric, ascorbic, butyric, lactic, tartaric, malic, fumaric, succinic and valeric.

In some embodiments, the compounds are in a therapeutically effective amount. In some embodiments, the therapeutically effective amount is sufficient to prevent, alleviate or ameliorate symptoms of a disease or to prolong the survival of the subject being treated. Determination of a therapeutically effective amount is well within the capability of those skilled in the art.

The compositions can include other active compounds to obtain desired combinations of properties. In a method and/or composition described herein can include another pharmacological agent known in the general art to be of value in treating one or more of the diseases or medical conditions referred to hereinabove, such as diseases or disorders associated with AR activity or in which AR activity is implicated. It is to be understood that such combination therapy constitutes a further aspect of the compositions and methods of treatment provided herein.

In some embodiments, a method and/or composition provided herein can be useful for treating a conditions or disorder in a mammalian, and particularly in a human subject. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In some embodiments, the compositions can be administered to achieve local rather than systemic exposures. For example, compositions can be injected directly in the area of desired effect (e.g., in the renal or cardiac area). In some embodiments in which the composition is administered locally, the dosage regimen can be adjusted to achieve a desired local concentration of a compound(s) provided herein.

In some embodiments, a composition provided herein can be administered in the form of a dosage unit (e.g., tablet, capsule, pill, injection, and bolus). In some embodiments, such dosage units include a composition provided herein in a dose from about or 0.01 µg/kg of body weight to about or 50 mg/kg of body weight per active ingredient. In other embodiments, such dosage units include a composition in a dose from about or 0.05 µg/kg of body weight to about or 40 mg/kg of body weight per active ingredient. In still other embodiments, such dosage units include a composition in a dose from about or 0.1 µg/kg of body weight to about or 30 mg/kg of body weight per active ingredient. In yet still other embodiments, such dosage units include a composition in a dose from about or 0.5 µg/kg of body weight to about or 25 mg/kg of body weight per active ingredient. In some embodiments, such dosage units include a composition in a dose from about or 1 µg/kg of body weight to about or 20 mg/kg of body weight per active ingredient. In other embodiments, such dosage units include a composition in a dose from about or 2 µg/kg of body weight to about or 15 mg/kg of body weight per active ingredient. In still other embodiments, such dosage units include a composition in a dose from about or 10 µg/kg of body weight to about or 5 mg/kg of body weight per active ingredient. In some embodiments, such dosage units includes a composition in a dose from about or 0.01 mg/kg of body weight to about or 1 mg/kg of body weight per active ingredient. In other embodiments, such dosage units includes a composition in a dose from about or 0.05 mg/kg of body weight to about or 0.1 mg/kg each of body weight per active ingredient. In yet still other embodiments, such dosage units include a composition of the hormone therapies in a dose from about or 0.001 µg/kg of body weight to about or 100 µg/kg of body weight per active ingredient. In some embodiments, such dosage units includes a composition described herein in a dose from about or 0.01 µg/kg of body weight to about or 10 µg/kg of body weight per active ingredient. In other embodiments, such dosage units includes a composition described herein in a dose from about or 0.1 µg/kg of body weight to about or 1 µg/kg each of body weight per active ingredient. An approximate average adult body weight is 70 kg. Thus, for an adult of average body weight, a dose of 0.1 µg/kg of body weight is equivalent to 7 µg, a dose of 1 µg/kg of body weight is equivalent to 70 µg, a dose of 10 µg/kg of body weight is equivalent to 700 µg or 0.7 mg and a dose of 0.1 mg/kg of body weight is equivalent to 7 mg.

In some embodiments, a composition can be administered as needed, once per week, once per day, twice per day, three times per day, or four or more times per day. It is recognized by those skilled in the art that the particular dose, frequency, and duration of administration depends on a number of factors, including, without limitation, the biological activity desired, the condition of the subject, and tolerance for the pharmaceutical composition.

Dosage amount, interval between doses, and duration of treatment can be adjusted to achieve a desired effect. In some embodiments, dosage amount and interval between doses are adjusted to maintain a desired concentration of compound in a subject. For example, in some embodiments, dosage amount and interval between doses are adjusted to provide plasma concentration of a compound provided herein at an amount sufficient to achieve a desired effect. In some of such embodiments the plasma concentration is maintained above the minimal effective concentration (MEC). In some embodiments, compositions provided herein can be administered with a dosage regimen designed to maintain a concentration above the MEC for 10-90% of the time, between 30-90% of the time, or between 50-90% of the time.

1. Oral Administration

In some embodiments, oral pharmaceutical dosage forms are either solid, gel or liquid. The solid dosage forms are tablets, capsules, granules, and bulk powders. Types of oral tablets include compressed, chewable lozenges and tablets which can be enteric coated, sugar coated or film coated. Capsules can be hard or soft gelatin capsules, while granules and powders can be provided in non-effervescent or effervescent form with the combination of other ingredients known to those skilled in the art.

In some embodiments, the formulations are solid dosage forms, such as capsules or tablets. The tablets, pills, capsules, troches and other solid dosage forms can include any of the following ingredients, or compounds of a similar nature: a binder; a diluent; a disintegrating agent; a lubricant; a glidant; a sweetening agent; and a flavoring agent.

In some embodiments, compositions for oral administration are push fit capsules made of gelatin. Certain of such push fit capsules include one or more compounds provided herein in admixture with one or more fillers such as lactose, binders such as starches, and/or lubricants such as talc or magnesium stearate and, optionally, stabilizers. In some embodiments, compositions for oral administration are soft, sealed capsules made of gelatin and a plasticizer, such as glycerol or sorbitol. In certain soft capsules, one or more compounds provided are be dissolved or suspended in suitable liquids, such as fatty oils, liquid paraffin, or liquid polyethylene glycols. In addition, stabilizers can be added.

In other embodiments, compositions are prepared for buccal administration. Certain of such compositions are tablets or lozenges formulated in conventional manner. In some embodiments, the compositions are formulated as dissolvable films, such as those made with pullulan or described in the art (e.g., see U.S. Pat. Nos. 6,596,298, 7,067,116, 7,182,964, and 7,241,411).

Examples of binders for use in the compositions provided herein include microcrystalline cellulose, gum tragacanth, glucose solution, gum arabic, gelatin solution, sucrose and starch paste. Lubricants include talc, starch, magnesium or calcium stearate, lycopodium and stearic acid. Diluents include, for example, lactose, sucrose, starch, kaolin, salt, mannitol, and dicalcium phosphate. Glidants include, but are not limited to, colloidal silicon dioxide. Disintegrating agents include croscarmellose sodium, sodium starch glycolate, alginic acid, sodium alginate, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol, xylitol and artificial sweetening agents such as saccharin. Flavoring agents include natural flavors extracted from plants such as fruits and synthetic blends of compounds which produce a pleasant sensation, such as, but not limited to peppermint and methyl salicylate, including spray dried natural and artificial flavors. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

When the dosage unit form is a capsule, it can include, in addition to material of the above type, a liquid carrier such as fatty oil. In addition, dosage unit forms can include various other materials which modify the physical form of the dosage unit, for example, coatings of sugar and other enteric agents. The compounds also can be administered as a component of an elixir, suspension, syrup, wafer, sprinkle or chewing gum. A syrup can include, in addition to the active compounds, sucrose as a sweetening agent and certain preservatives, dyes and colorings and flavors.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents also can be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Tablets and capsules formulations can be coated as known by those of skill in the art in order to modify or sustain dissolution of the active ingredient. Thus, for example, they can be coated with a conventional enterically digestible coating, such as phenylsalicylate, waxes and cellulose acetate phthalate.

Exemplary compositions can include fast-dissolving diluents such as mannitol, lactose, sucrose, and/or cyclodextrins. Also included in such formulations can be high molecular weight excipients such as celluloses and microcrystalline celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers also can be added for ease of fabrication and use.

In some of such embodiments, a composition for oral administration can be formulated by combining two or more compounds provided herein with one or more pharmaceutically acceptable carriers. Certain of such carriers enable compounds provided herein to be formulated in dosage forms, such as tablets, pills, dragees, capsules, liquids, gels, syrups, slurries and suspensions, for oral ingestion by a subject. In some embodiments, compositions for oral use can be obtained by mixing two or more active compounds provided herein and one or more solid excipient. Suitable excipients include, but are not limited to, fillers, such as sugars, including lactose, sucrose, mannitol, or sorbitol;

cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). In certain embodiments, such a mixture is optionally ground and auxiliaries are optionally added. In some embodiments, compositions can be formed to obtain tablets or dragee cores. In some embodiments, disintegrating agents (e.g., cross linked polyvinyl pyrrolidone, agar, or alginic acid or a salt thereof, such as sodium alginate) are added.

In some embodiments, dragee cores are provided with coatings. In some of such embodiments, concentrated sugar solutions can be used, which can optionally include gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to tablets or dragee coatings.

In some embodiments, a daily dosage regimen for a subject includes an oral dose of between 0.1 μg and 2000 mg the compositions provided herein. In certain embodiments, a daily dosage regimen for a subject includes an oral dose of between 1 μg and 500 mg of the compositions provided herein. In some embodiments, a daily dosage regimen for a subject includes an oral dose of between 10 μg and 100 mg of the compositions provided herein. In certain embodiments, a daily dosage regimen for a subject includes an oral dose selected from among 0.01, 0.05, 0.075, 0.1, 0.25, 0.5, 0.75, 1, 2, 2.5, 3, 4, 5, 6, 7, 8, 9, 10, 15, 20, 25, 50, 75, 100, 125, 150, 175, 180, 190, 200, 225, 250, 300, 400, 500, 750, 800, 850, 900, 950 and 1000 milligrams of the compositions provided herein. In some embodiments, a daily dosage regimen can be administered as a single daily dose. In other embodiments, a daily dosage regimen can be administered as two, three, four, or more than four doses.

2. Injectables, Solutions and Emulsions

In some embodiments, the composition can be prepared for transmucosal administration. In some of such embodiments penetrants appropriate to the barrier to be permeated are used in the formulation. Such penetrants are generally known in the art.

Parenteral administration, generally characterized by injection, either subcutaneously, intramuscularly or intravenously also is contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol, mannitol, 1,3-butanediol, Ringer's solution, an isotonic sodium chloride solution or ethanol. In addition, if desired, the pharmaceutical compositions to be administered also can include minor amounts of non-toxic auxiliary substances such as wetting or emulsifying agents, pH buffering agents, stabilizers, solubility enhancers, and other such agents, such as for example, mono- or diglycerides, fatty acids, such as oleic acid, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) also is contemplated herein. Briefly, a compound provided herein is dispersed in a solid inner matrix, e.g., polymethyl-methacrylate, polybutylmethacrylate, plasticized or unplasticized polyvinylchloride, plasticized nylon, plasticized polyethylene-terephthalate, natural rubber, polyisoprene, polyisobutylene, polybutadiene, polyethylene, ethylene-vinylacetate copolymers, silicone rubbers, polydimethyl-siloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxy-ethanol copolymer, that is insoluble in body fluids. The compound(s) diffuses through the outer polymeric membrane in a release rate controlling step. The percentage of active compounds included in such parenteral compositions is highly dependent on the specific nature thereof, as well as the activity of the compounds and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or PBS, and solutions including thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Anti-oxidants include sodium bisulfate. Local anesthetics include procaine hydrochloride. Suspending and dispersing agents include sodium carboxymethylceluose, hydroxy-propyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the subject or animal as is known in the art.

The unit dosage parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution including an active compound is an effective mode of administration. Another embodiment is a sterile aqueous or oily solution or suspension including an active material injected as necessary to produce the desired pharmacological effect.

Injectables are designed for local and systemic administration. Typically a therapeutically effective dosage is formulated to include a concentration of at least about 0.1% w/w up to about 90% w/w or more, in some embodiments more than 1% w/w, of the active compounds to the treated tissue(s). The active ingredient can be administered at once, or can be divided into a number of smaller doses to be administered at intervals of time. The precise dosage and duration of treatment is a function of the tissue being treated and can be determined empirically using known testing protocols or by extrapolation from in vivo or in vitro test data. It is to be noted that concentrations and dosage values also can vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of formulations provided herein.

The compositions can be formulated in any suitable vehicle or form. For example, they can be in micronized or other suitable form and/or can be derivatized to produce a more soluble active product or to produce a prodrug or for other purposes. The form of the resulting mixture depends upon a number of factors, including, for example, an intended mode of administration and the solubility of the compound in the selected carrier or vehicle. The effective concentration is sufficient for ameliorating the symptoms of the condition and can be empirically determined.

In some embodiments, a composition can be prepared for administration by injection wherein the composition includes a carrier and is formulated in aqueous solution, such as water or physiologically compatible buffers such as Hanks's solution, Ringer's solution, or physiological saline buffer. In some embodiments, other ingredients are included (e.g., ingredients that aid in solubility or serve as preservatives). In some embodiments, injectable suspensions are prepared using appropriate liquid carriers and/or suspending agents. Certain compositions for injection are presented in unit dosage form, e.g., in ampules or in multi dose containers. Certain compositions for injection are suspensions, solutions or emulsions in oily or aqueous vehicles, and can include formulatory agents such as suspending, stabilizing and/or dispersing agents. Certain solvents suitable for use in compositions for injection include, but are not limited to, lipophilic solvents and fatty oils, such as sesame oil, synthetic fatty acid esters, such as ethyl oleate or triglycerides, and liposomes. Aqueous injection suspensions can include substances that increase the viscosity of the suspension, such as sodium carboxymethyl cellulose, sorbitol, or dextran. Optionally, such suspensions also can include suitable stabilizers or agents that increase the solubility of the compounds to allow for the preparation of highly concentrated solutions.

In some embodiments, the composition can be prepared for administration by inhalation. Certain of such compositions for inhalation are prepared in the form of an aerosol spray in a pressurized pack or a nebulizer. Certain of such compositions include a propellant, e.g., dichlorodifluoromethane, trichlorofluoromethane, dichlorotetrafluoroethane, carbon dioxide or other suitable gas. In certain embodiments using a pressurized aerosol, the dosage unit can be determined with a valve that delivers a metered amount. In some embodiments, capsules and cartridges for use in an inhaler or insufflator can be formulated. Certain of such formulations include a powder mixture of a compound provided herein and a suitable powder base such as lactose or starch.

In some embodiments, the compositions can be administered by continuous intravenous infusion. In some of such embodiments, from 0.01 μg to 500 mg of the composition is administered per day.

3. Lyophilized Powders

Of interest herein also are lyophilized powders, which can be reconstituted for administration as solutions, emulsions and other mixtures. They also can be reconstituted and formulated as solids or gels.

The sterile, lyophilized powder is prepared by dissolving a composition provided herein, or a pharmaceutically acceptable derivatives thereof, in a suitable solvent. The solvent can include an excipient which improves the stability or other pharmacological component of the powder or reconstituted solution, prepared from the powder. Excipients that can be used include, but are not limited to, dextrose, sorbitol, fructose, corn syrup, xylitol, glycerin, glucose, sucrose or other suitable agent. The solvent also can include a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. In some embodiments, each vial includes a single dosage of from 10 μg to 1000 mg of the compositions. In another embodiment, each vial includes a single dosage of from 100 μg to 500 mg of the compositions. In another embodiment, each vial includes a single dosage of from 0.1 mg to 50 mg. In another embodiment, each vial includes a single dosage of from 0.05 mg to 20 mg. In another embodiment, each vial includes a single dosage of 0.1 mg, 0.25 mg, 0.5 mg, 1 mg, 2 mg, 3 mg, 4 mg, 5 mg, 6 mg, 7 mg, 8 mg, 9 mg or 10 mg. In another embodiment, each vial includes multiple dosages of the compositions. The lyophilized powder can be stored under appropriate conditions, such as at about 4° C. to room temperature.

Reconstitution of this lyophilized powder with water for injection provides a formulation for use in parenteral administration. For reconstitution, about 1 mg to 50 mg of the compositions is added per mL of sterile water or other suitable carrier. In some embodiments, 5 mg to 35 mg of the compositions is added per mL of sterile water or other suitable carrier. In other embodiments, 10 mg to 30 mg of lyophilized powder is added per mL of sterile water or other suitable carrier. The precise amount depends upon the selected compounds. Such amount can be empirically determined.

4. Topical Administration

Topical mixtures are prepared as described for the local and systemic administration. The resulting mixture can be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration. Transdermal skin patches useful for administering the compounds disclosed herein include those well known to those of ordinary skill in that art.

The compounds or pharmaceutically acceptable derivatives thereof can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, in some embodiments less than 10 microns.

In some embodiments, the compositions for inhalation can be prepared in the form of an aerosol spray in a pressurized pack or a nebulizer. Certain of such compositions include a propellant, e.g., dichlorodifluoro-methane, trichloro-fluoromethane, dichlorotetrafluoroethane, carbon dioxide or other suitable gas. In some embodiments using a pressurized aerosol, the dosage unit can be determined with a valve that delivers a metered amount. In some embodiments, capsules and cartridges for use in an inhaler or insufflator can be formulated. Certain of such formulations include a powder mixture of a compound provided herein and a suitable powder base such as lactose or starch.

Exemplary compositions for nasal aerosol or inhalation administration include solutions that can include, for example, benzyl alcohol or other suitable preservatives, absorption promoters to enhance absorption and/or bioavailability, and/or other solubilizing or dispersing agents such as those known in the art.

The compositions can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients also can be administered. These solutions, particularly those intended for ophthalmic use, can be formulated as 0.01%-10% isotonic solutions, pH about 5-7, with appropriate salts. In certain embodiments in which the compositions are administered locally, the dosage regimen is adjusted to achieve a desired local concentration of the compositions provided herein.

In some embodiments, the composition can be prepared for topical administration. Certain of such compositions include bland moisturizing bases, such as ointments or creams. Any of the ointment bases known in the art, including water in oil emulsion bases, oil in water emulsion bases, absorption bases, oleaginous bases and water soluble or water miscible bases can be used (e.g., see Remington: The Science and Practice of Pharmacy, 19th Ed. (Easton, Pa.: Mack Publishing Co., 1995) at pages 1399-1404). Oleaginous ointment bases are generally anhydrous and include, for example, vegetable oils, animal fats, and semisolid petroleum-based hydrocarbons. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin, stearic acid and polyethylene glycols of varying molecular weight. Creams are viscous liquids or semi-solid emulsions, and can be either oil-in-water or water-in-oil emulsions. Cream bases are water-washable, and contain an oil phase, an emulsifier, and an aqueous phase, which can include a fatty alcohol. The emulsifier in a cream formulation is generally a nonionic, anionic, cationic, or amphoteric surfactant. Lotions are preparations to be applied to the skin surface without friction, and often include a water or alcohol base, and include an emulsion and often solid particles (such as cocoa butter or fatty acid alcohols).

Exemplary suitable ointment bases include, but are not limited to, petrolatum, petrolatum plus volatile silicones, and lanolin. Cream bases, such as those including an emulsion of water, a mineral oil or petrolatum, one or more fatty alcohols or fatty esters, a polyoxyethylene ether or ester surfactant or polysorbate surfactant, also can be used. Exemplary suitable cream bases include, but are not limited to, cold cream (USP), hydrous lanolin and hydrophilic ointment (USP). The moisturizing bases can further contain various other emollients, emulsifiers, perfumes, colorants and preservatives.

Suitable water-in-oil emulsions are commercially available, e.g., blends of petrolatum, mineral oil, ceresin, lanolin alcohol, panthenol, glycerin and bisabolol under the designation Aquaphor™, available from Beiersdorf Futuro Inc. (Cincinnati, Ohio); blends of water, glycerin, panthenol, caprylic/capric triglyceride, dicaprylyl carbonate, octyl-dodecanol, C12-15 alkyl benzoate, dimethicone, squalane, tapioca starch, cetearyl alcohol, glyceryl stearate citrate, myristyl myristate, butylene glycol, benzyl alcohol, carbomer, phenoxyethanol, ammonium acryloyldimethyltaurate/VP copolymer, sodium hydroxide, methylparaben, propylparaben, iodopropynl butylcarbamate, such as Eucerin™, available from Beiersdorf Futuro Inc. (Cincinnati, Ohio), blends of water, mineral oil, petrolatum, glycerin, isohexadecane, microcrystalline wax, lanolin alcohol, paraffin, panthenol, magnesium sulfate, decyl oleate, octyldodecanol, aluminum stearate, methylchloro-isothiazolinone, methylisothiazolinone, citric acid and magnesium stearate, such as Nivea™ Cream, available from Beiersdorf Futuro Inc. (Cincinnati, Ohio).

Suitable oil-in-water emulsions are commercially available, e.g., water, mineral oil, petrolatum; sorbitol, stearic acid, lanolin, lanolin alcohol, cetyl alcohol, glyceryl stearate/PEG-100 stearate, triethanolamine, dimethicone, propylene glycol, microcrystalline wax, tri(PPG-3 myristyl ether) citrate, disodium EDTA, methylparaben, ethylparaben, propyl-paraben, xanthan gum, butylparaben and methyldibromo glutaronitrile, such as Lubriderm™ Cream, available from Pfizer (Morris Plains, N.J.); a blend of purified water, petrolatum, mineral oil, cetstearyl alcohol, propylene glycol, sodium laurel sulfate, isopropyl palmitate, imidazolidinyl urea, methylparaben and propylparaben, such as Dermabase™ cream, available from Paddock Industries, Inc. (Minneapolis, Minn.); and a blend of purified water, glycerin, hydrogenated polyisobutene, cetearyl alcohol and ceteareth-20, macadamia nut oil, dimethicone, tocopheryl acetate, stearoxytrimethylsilane (and) stearyl alcohol, panthenol, farnesol, benzyl alcohol, phenoxyethanol, acrylates/C10-30 alkyl acrylate crosspolymer, sodium Hydroxide and citric acid, such as Cetaphil™ lotion, available from Galderma Laboratories (Ft. Worth, Tex.).

In some embodiments, the formulation, route of administration and dosage for the composition provided herein can be chosen in view of a particular subject's condition (see e.g., Fingl et al., "The Pharmacological Basis of Therapeutics", Chapter 1, p. 1 (1975)). In certain embodiments, the pharmaceutical composition is administered as a single dose. In certain embodiments, a pharmaceutical composition is administered as a series of two or more doses administered over one or more days.

5. Other Routes of Administration

In some embodiments, the composition can be prepared for topical administration, such as rectal administration. The dosage forms for rectal administration include, but are not limited to rectal suppositories, retention enema, capsules and tablets for systemic effect. For rectal administration, certain pharmaceutical agents can be included, known ingredients, such as cocoa butter and/or other glycerides. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases can be used. In certain embodiments, the pharmaceutical compositions include moisturizing bases, such as ointments or creams. Agents to raise the melting point of suppositories include spermaceti and wax. Rectal suppositories can be prepared either by the compressed method or by molding. The typical weight of a rectal suppository is about 2 to 3 gm.

Tablets and capsules for rectal administration are manufactured using the same pharmaceutically acceptable substances and by the same methods as for formulations for oral administration.

In some embodiments, the compounds of a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing, or a method and/or composition that includes an effective amount of lasofoxifene, or a pharmaceutically acceptable salt, ester or prodrug of the foregoing) can be provided via oral administration, rectal administration, transmucosal administration, intestinal administration, enteral administration, topical administration, transdermal administration, intrathecal administration, intraventricular administration, intraperitoneal administration, intranasal administration, intraocular administration and/or parenteral administration.

C. EVALUATION OF THE ACTIVITY

Standard physiological, pharmacological, and biochemical procedures are available for testing the compounds of the compositions provided herein to identify those that possess activity as SERMs, 5α-reductase inhibitors, SARMs or ER modulating compounds. In vitro and in vivo assays known in the art can be used to evaluate the activity of the compound classes provided herein. For example, SERMs, SARMs, and ER modulating compounds can be identified using a series of in vitro cotransfection assays that profiles ligand mediated modulation of AR or ER including subtypes (e.g., see U.S. Pat. No. 7,196,076; J. Rosen, et al. J Med Chem 38: 4855-74 (1995)). In some embodiments, a method and/or composition described herein (e.g., a method and/or composition that includes a combination of an effective amount of a selective estrogen receptor modulator and an effective amount of a 5α-reductase inhibitor, or a pharmaceutically acceptable salt, ester or prodrug of the foregoing, or a method and/or composition that includes an effective amount of a selective androgen receptor modulator compound and an effective amount of an estrogen receptor modulator, or a pharmaceutically acceptable salt, ester or prodrug of the foregoing) can be capable of modulating activity of androgen or estrogen receptors in the cotransfection assays with agonist $EC_{50}$ and antagonist $IC_{50}$ values of less than 1 micromolar. In some embodiments, the $EC_{50}$ and $IC_{50}$ values can be in the range of less than 100 nM. In some embodiments, the $EC_{50}$ and $IC_{50}$ values can be in the range of less than 10 nM.

The binding of the SERMs, SARMs and ER modulating compounds, and the inhibition activity of 5α-reductase inhibitors provided herein to their target receptors or of the enzymes can be assessed using any method known in the art. For examples, a baculovirus expression plasmid including cDNA encoding the human steroidal hormone receptor protein (AR, PR, GR, MR, or ER) can be prepared using standard techniques to measure competitive binding affinity of the compounds to the steroid receptors against the radiolabeled nature ligands of the receptors (e.g., see Allegretto et al., *J. Biol. Chem.* 268: 26625 (1993)), and a 5α-reductase assay using human tissue to isolate the 5α-reductase enzymes can be used to measure the inhibition activities of compounds (e.g. see US Pat. App. No. 2009/0123571). In some embodiments, the compounds of the SERMs, SARMs and ER modulators provided herein can exhibit a binding $K_i$, and 5α-reductase inhibitors provided herein can exhibit a $IC_{50}$ of no greater than 1 micromolar, or no greater than 100 nanomolar, or no greater than 10 nanomolar or no greater than 1 nanomolar in an receptor binding or enzyme inhibition assays.

Certain advanced in vivo models are available to assess the benefit/risk profile. Ovariectomized mature female rat model is available to characterize primarily bone activity. Intact cynomolgus monkey model is available to assess of the effects on hypothalamic-pituitary-gonadal axis and lipid profile.

D. EXAMPLES

The following examples, including experiments and results achieved, are provided for illustrative purposes only and are not to be construed as limiting the claimed subject matter.

Example 1—Ovariectomized Mature Female Rat Model

Ovariectomized mature female rats are used to characterize primarily bone activity of the compositions provided herein or the individual SERM or SARM compounds. A sham group is used as control. The model can be run in either maintenance mode where the animals are dosed one day after the ovariectomy or restoration mode where the animals are dosed seven to eight weeks after the surgery. The rats are scanned by dual energy x-ray absorptiometry and sorted into experimental groups based upon femoral bone mineral content (BMC). Three dosages of testing compositions/compounds are administered orally once a day for 4, 8, or 12 weeks and estradiol and testosterone are administered subcutaneously to the reference groups. Animals received subcutaneous injections of fluorochrome markers for bone histomorphometric analysis. Alizarian Red S was prepared as a 3% solution and given at a dose of 30 mg/kg at the time of the baseline scan. Calcein was administered 10 days and 3 days prior to necropsy.

Approximately 24 hours after the last dose, blood is collected and the gastrocnemius muscle, plantaris muscle, uterus, clitoral glands, clitoris and inguinal fat pads were isolated, blotted and weighed individually. The left femur and lumbar vertebra L5 are wrapped in saline-soaked gauze and stored at −20° C. for biochemical analysis. The right femur and lumbar vertebrae L3-L4 are collected and stored in 70% ethanol for histomorphometry. The right tibia is collected in formalin for histological analysis. The left tibia is collected on dry ice and stored at −20° C. for measurement of alkaline phosphatase activity.

BMC, bone mineral density (BMD) and bone length are measured by pDEXA on an entire femur. The coefficient of variation for repeated measurement of the isolated femur is less than 0.4% for the BMC and the BMD measurements. Estradiol significantly increases femur BMD at 0.1 mg/kg/day. Serum osteocalcin, a marker for bone turnover, and alkaline phosphatase derived from the tibial periosteum are also measured. Whole femurs are collected for biomechanical analysis and thawed at room temperature prior to testing. Peak load and peak displacement are measured directly from the load cell and the crosshead, respectively. Stiffness is calculated from the slope of the linear region of the load/displacement curve. Lumbar vertebra L5 is also measured in the mechanical testing for bone strength. Testosterone increases bending stiffness but does not significantly increase bending strength. Estradiol does not have a significant effect on biomechanical properties at the femur but significantly increases lumbar spine compressive strength and stiffness.

Bone histomorphometry is performed to indicate growth of the new bone during the study. The section from the lumbar vertebral bodies is used for histomorphometric indices of cancellous bone, while the sections of the femur mid-shafts are used for histomorphometric indices of cortical bone.

Body weight, gastrocnemius weight and plantaris weight changes are measured indicating anabolic activity of the testing compositions/compounds on skeletal muscle. Inguinal fat pad weight is used as a representative fat pad to assess the effects of the testing compounds on body fat. Clitoral gland and clitoral weights are measured to assess the virilizing effect of drugs. Testosterone propionate significantly increases clitoral gland and clitoral weights at 1 mg/kg daily dose.

In the maintenance node of this model, (5R,6S)-6-phenyl-5-[4-(2-pyrrolidin-1-ylethoxy)phenyl]-5,6,7,8-tetrahydronaphthalen-2-ol (Compound 1) was dosed daily at 0 (sham), 0 (OVX), 0.01, 0.05, and 0.25 mg/kg for 8 weeks and 17α-ethynylestradiol was dosed at 0.03 mg/kg/day. Uterine wet weight decrease after OVX surgery is completely blocked by estrogen treatment and Compound 1 at all doses are also block the decrease but at much less extend. Micro-computerized tomography (uCT) measured the density and connectivity of the trabecular bone in the femur and pQCT measured at the distal femur. Both estrogen and Compound 1 treatment prevent the bone density decrease caused by OVX by the two different measurements. Similar results were obtained by bone histomorphometry measurement of the proximal and bone strength measurement on the lumbar vertebrae that Compound 1 maintained the bone strength after 8 weeks daily dosing.

In the restoration mode of this osteopenic female rat model, 4-(2(R)-(1(S)-hydroxyl-2,2,2-trifluoroethyl)-pyrrolidinyl)-2-trifluoromethylbenzonitrile (Compound 2, Formula I, $R^1=CF_3$, $R^2=R^3=H$) was dosed at 0 (sham), 0 (OVX), 0.03, 0.3, and 3 mg/kg orally for 12 weeks. Compound 2 significantly increased cortical bone mass, density, strength, stiffness and periosteal bone formation rates. These changes demonstrate that the compound has anabolic activity at cortical bone sites and are inconsistent with a compound that predominately inhibits resorption, such as estradiol. Compound 2 suppressed cancellous bone turnover while increasing trabecular bone volume and increasing bone mineral density at the lumbar spine. In addition to the effects on bone, Compound 2 increased gastrocnemius muscle weight, plantaris muscle weight and body weight without affecting inguinal fat pad weight. The tissue selectivity was also demonstrated, as it was more efficacious on muscle and bone at the 0.3 mg/kg/day dose than testosterone, yet has reduced activity on the clitoral gland, clitoris or uterus relative to testosterone.

In the same experiment of Compound 2, another SARM compound, ostarine, was dosed at 0.03, 0.3, and 3 mg/kg/day orally for 12 weeks. Ostarine showed activity on bone and muscle as well as tissue selectivity similar to that of Compound 2, although ostarine had decreased potency, reaching maximal efficacy at an exposure substantially higher level (~10-fold of Compound 2).

Example 2—Orchidectomized Mature Male Rat Model

The orchidectomized male Sprague-Dawley rat model is used to assess the effects of the compositions provided herein or the individual SARM compounds on various reproductive, gonadotropin and musculoskeletal endpoints, including sex accessory organs, bone, serum gonadotropin levels and striated muscle in mature male rats. This model can be run in the maintenance mode where the animals are dosed one day after the orchidectomy or in the restoration mode where the animals are dosed 14 days after the surgery.

After 1 or 14 days from the orchidectomy surgery, animals are sorted into groups based on mean body weights and received treatment of testing articles for 14 days. Sham-operated and orchidectomized rats are treated with vehicle served as controls. After the $14^{th}$ dose, venous blood is collected at 0, 1, 2, 4 and 6 hours after dosing. The blood samples are collected in EDTA-containing tubes. Approximately 24 hours after the last dose, animals are euthanized and seminal vesicle weights, ventral prostate weights, levator ani weights, preputial gland weights and blood samples are collected on necropsy. Serum samples are assayed for LH, T, osteocalcin, and test compounds.

Orchidectomy removes almost all of the endogenous circulating androgens in the rat. When administered at an efficacious dose, the compositions/compounds are able to maintain levator ani weight at sham-equivalent levels, while the same dose does not maintain the growth of ventral prostate or seminal vesicle at sham-equivalent level. At the higher doses, the testing article significantly increased levator ani weight above sham-equivalent levels, but still only restores the ventral prostate or seminal vesicles to 50% or less of sham levels.

In the restoration mode of the model, Compound 2 was dosed at 0 (sham), 0 (ORDX), 0.03, 0.1, 0.3, 1, 3, 10, 30, and 100 mg/kg/day for 14 days and exhibited positive activity in musculoskeletal endpoints. Compound 2 had dose proportional exposure and maintained levator ani weight at sham-equivalent levels at a dose of 2 mg/kg/day (AUC$_{24}$: 0.2 µg·/mL). At doses that maintained levator ani weights at sham equivalent levels, Compound 2 had lower efficacy (relative to sham) in sex accessory and sebaceous glands. Compound 2 also showed tissue selective activity toward the muscle endpoint. Compound 2 showed lower potency for reducing the elevated LH levels in castrate rats (≥10 mg/kg/day) compared to increasing the reduced levator ani skeletal muscle mass in these animals (2 mg/kg/day). Compound 2 suppressed serum LH below sham-equivalent levels at high doses.

In the same study of Compound 2, ostarine was dosed at 0.03, 0.1, 0.3, 1, 3, 10, 30, and 100 mg/kg/day for 14 days and had efficacy and high tissue selectivity similar to that of Compound 2, although ostarine had ~10-fold less potency based on AUC-activity relationship analysis.

Example 3—Intact Cynomolgus Monkey Model

Intact cynomolgus male and female monkeys are used to assess of the effects of the compositions provided herein or the individual SERM or SARM compounds on hypothalamic-pituitary-gonadal axis and lipid profile. All animals are dosed via oral or nasol gavage once daily for consecutive days with either vehicle or testing articles of different doses. The first day of dosing is designated Day 1 for all animals. Blood samples are collected for analysis of LH, FSH, T, Estrodiol, total cholesterol, triglycerides, cortisol, and coagulation parameters included prothrombin time (PT) and activated partial thromboplastin time on Days -3 and end of the study.

In this model, Compound 2 was dosed at 0, 5, 50, 150, and 450 mg/kg/day for 14 days. On Day 14, serum cholesterol decreased in both males and females in 17%, 71%, 81%, 79%, and 84% of the corresponding Day -3 values for the 5 dosing groups without dose dependent changes in triglycerides. On Day 14, all animals in compound-dosed groups, except for the 5 mg/kg-dosed female, had minimally prolonged (1.8 to 3.5 seconds longer than Day -3) prothrombin time (PT); PT in the control animals was similar to Day -3. In a separate study, the compound was dosed at 0, 3, 10, 30, 120, and 500 mg/kg/day for 30 days. The compound has a suppressive effect on the hypothalamic-pituitary-gonadal axis in female and male monkeys. Serum estradiol and serum FSH were significantly suppressed in females. Serum testosterone was suppressed in males as indicated by lower 75th, 50th, and 25th percentile values in samples from treated monkeys than vehicle controls. Serum FSH was not significantly altered.

In this model, Compound 1 was dosed at 0, 1, 5, and 15 mg/kg/day for 3 months. On Day 90, serum cholesterol did not change in males and slightly increased in females in 3.7%, 26%, 16%, and 7.8% of the corresponding Day -7 values for the 4 dosing groups with significant increase in triglycerides, especially in males.

Example 4—Stimulation of Endogenous Testosterone Production in Men

In a random, double-blind, placebo controlled study, Compound 1 was given orally to healthy male subjects age from 18 to 45 years. Subjects received either placebo or Compound 1 under fasted/fed conditions at single escalating doses of 0, 1, 3, 10, 30, and 100 mg. Total serum T level was determined at days 0, 1, 7, 14, 21, and 28. The results in Table 1 clearly show a dose related increase of T level with a single dose of the compound and the elevation lasted at least 28 days.

TABLE 1

Changes of T levels from baseline

| Cohort | Baseline (nM) | Day 1 2 h | Day 1 12 h | Day 8 | Day 15 | Day 22 | Day 29 |
|---|---|---|---|---|---|---|---|
| Placebo fasted | 17.25 | 7.6% | -29% | 19% | 1.0% | -0.4% | 12% |
| Placebo fed | 13.05 | — | -39% | 21% | 4.6% | -1.5% | -1.9% |
| 1 mg fasted | 13.65 | 9.9% | — | — | — | — | 18% |
| 3 mg fasted | 14.38 | 13% | — | — | — | 68% | 50% |
| 10 mg fasted | 19.83 | -0.5% | — | — | 67% | 81% | 29% |
| 30 mg fasted | 18.28 | -6.9% | -64% | 39% | 71% | 78% | 81% |
| 100 mg fasted | 18.55 | ND | -50% | 84% | 104% | 92% | 114% |
| 100 mg fed | 15.50 | ND | -48% | 86% | 89% | 110% | 91% |

"—" Means not measured.

Since modifications will be apparent to those of skill in this art, it is intended that this invention be limited only by the scope of the appended claims.

The invention claimed is:

1. A method of treating a disease, disorder or condition by administering an effective amount of a selective androgen receptor modulator compound and an effective amount of an estrogen receptor modulator, or a pharmaceutically acceptable salt, ester or prodrug of the foregoing; and wherein the selective androgen receptor modulator is 4-(2(R)-(1(S)-hydroxy-2,2,2-trifluoroethyl)pyrrolidinyl)-2-trifluoromethyl-benzonitrile, or a pharmaceutically acceptable salt, ester or prodrug thereof;

wherein the estrogen receptor modulator is lasofoxifene; and where the disease, disorder, or condition is selected from the group consisting of aging skin; Alzheimer's disease; an anemia; anorexia; arthritis; gout; arteriosclerosis; atherosclerosis; bone disease; bone damage; bone fracture; distraction osteogenesis; reduced bone mass, reduced bone density; reduced bone growth; bone weakening induced by glucocorticoid administration; musculoskeletal impairment (e.g., in the elderly); cachexia; breast cancer and osteosarcoma; cardiac dysfunction; myocardial infarction; cardiac hypertrophy; congestive heart failure; cardiomyopathy; catabolic side effects of glucocorticoids; Crohn's disease; growth retardation in connection with Crohn's disease; short bowel syndrome; irritable bowel syndrome; inflammatory bowel disease; ulcerative colitis; cognitive decline; cognitive impairment; dementia; short term memory loss; COPD; chronic bronchitis; decreased pulmonary function; emphysema; decreased libido in men; decreased libido in women; depression; nervousness, irritability and/or stress; reduced mental energy and low self-esteem (e.g., motivation/assertiveness); dyslipidemia; erectile dysfunction; frailty; age-related functional decline ("ARFD") in the elderly; growth hormone deficiency; hematopoietic disorders; sex hormone deficiency (male and female); hyper-cholesterolemia; hyperinsulinemia; hyperlipidemia; hypertension; hyperandrogenemia; hypogonadism (including primary and secondary); hypothermia (including hypothermia following anesthesia); impotence; insulin resistance; type 2 diabetes; lipodystrophy; male menopause; metabolic syndrome (syndrome X); loss of muscle strength; loss of muscle strength function; muscular dystrophies; muscle loss following surgery; muscular atrophy; neurodegenerative diseases; neuromuscular disease; decreased platelet count; platelet aggregation disorders; obesity; osteoporosis; osteopenia; glucocorticoid-induced osteoporosis; osteochondrodysplasias; periodontal disease; premenstrual syndrome; postmenopausal symptoms in women; Reaven's syndrome; rheumatological disease; sarcopenia; male sexual dysfunction; female sexual dysfunction; erectile dysfunction; decreased sex drive; decreased libido; physiological short stature, including growth hormone deficient children and short stature associated with chronic illness and growth retardation associated with obesity; tooth damage; thrombocytopenia; vaginal dryness; atrophic vaginitis; ventricular dysfunction; and wasting.

2. The method of claim 1, wherein the disease, disorder or condition is selected from among muscular atrophy; osteoporosis; male sexual dysfunction; female sexual dysfunction; hypogonadism; frailty; cancer cachexia; and decreased libido.

3. The method of claim 1, wherein the treatment produces an effect selected from group consisting of improved bone strength, improved muscle strength; improved muscle tone; reduced subcutaneous fat in a subject; increased athletic performance; attenuation or reversal of protein catabolic responses following trauma; improved sleep quality; correction of the relative hyposomatotropism of senescence due to high increase in REM sleep and a decrease in REM latency; modification of lipid profile; correction of female androgen deficiency; and correction of male androgen decline.

4. The method of claim 1, wherein the disease, disorder or condition is selected from the group consisting of acanthosis *nigricans*; acne; adrenal hyperandrogenism; androgenetic alopecia (male-pattern baldness); BPH; breast cancer; bladder cancer; brain cancer; endometrium cancer; kidney cancer; lung (non-small cell lung) cancer; ovarian cancer; pancreatic cancer; skin cancer; lymphatic cancer; bulimia nervosa; chronic fatigue syndrome (CFS); chronic myalgia; acute fatigue syndrome; counteracting preeclampsia, eclampsia of pregnancy and preterm labor; delayed wound healing; erythrocytosis; gestational diabetes; hirsutism; hyper-insulinemia; nesidioblastosis; hyperandrogenism; hypercortisolism; Cushing's syndrome; hyperpilosity; menstrual irregularity; ovarian hyperandrogenism; polycystic ovarian syndrome; seborrhea; sleep disorders; sleep apnea; and visceral adiposity.

\* \* \* \* \*